United States Patent
Bharadwaj et al.

(10) Patent No.: US 6,566,573 B1
(45) Date of Patent: May 20, 2003

(54) AUTOTHERMAL PROCESS FOR THE PRODUCTION OF OLEFINS

(75) Inventors: Sameer S. Bharadwaj, Midland, MI (US); Joseph J. Maj, Midland, MI (US); Jonathan H. Siddall, Midland, MI (US); Mark D. Bearden, Lake Jackson, TX (US); Craig B. Murchison, Midland, MI (US); Gerald E. Lazaruk, Sanford, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 09/388,219

(22) Filed: Sep. 1, 1999

Related U.S. Application Data

(60) Provisional application No. 60/099,041, filed on Sep. 3, 1998, provisional application No. 60/111,861, filed on Dec. 11, 1998, and provisional application No. 60/136,003, filed on May 26, 1999.

(51) Int. Cl.$^7$ .......................... C07C 5/333; C07C 5/327; C07C 5/42
(52) U.S. Cl. .................. 585/658; 585/660; 585/656; 585/621; 585/624; 585/625
(58) Field of Search .................. 585/658, 660, 585/656, 621, 624, 625

(56) References Cited

U.S. PATENT DOCUMENTS

| | | | | |
|---|---|---|---|---|
| 2,606,159 A | * | 8/1952 | Owen | 502/259 |
| 3,143,490 A | * | 8/1964 | Brennan et al. | 208/49 |
| 3,270,080 A | * | 8/1966 | Christmann | 585/622 |
| 3,308,181 A | | 3/1967 | Pitzer | 260/680 |
| 3,584,060 A | | 6/1971 | Rausch | 260/669 |
| 3,670,044 A | | 6/1972 | Drehman et al. | 260/683.3 |
| 4,295,817 A | | 10/1981 | Caplin et al. | 431/7 |
| 4,551,574 A | | 11/1985 | Imai et al. | 585/660 |
| 4,652,687 A | | 3/1987 | Imai et al. | 585/314 |
| 4,788,371 A | | 11/1988 | Imai et al. | 585/443 |
| 4,844,837 A | | 7/1989 | Heck et al. | 252/373 |
| 4,886,926 A | | 12/1989 | Dessau et al. | 585/444 |
| 4,886,928 A | | 12/1989 | Imai et al. | 585/660 |
| 4,886,932 A | | 12/1989 | Leyshon | 585/500 |
| 4,897,253 A | | 1/1990 | Jenkins | 423/651 |
| 4,902,849 A | | 2/1990 | McKay et al. | 585/660 |
| 4,940,826 A | | 7/1990 | Freide et al. | 585/600 |
| 5,073,657 A | | 12/1991 | Warren | 585/500 |
| 5,105,052 A | | 4/1992 | Freide et al. | 585/651 |
| 5,139,993 A | | 8/1992 | Schmidt et al. | 502/375 |
| 5,258,567 A | | 11/1993 | Kerby et al. | 585/654 |
| 5,306,684 A | | 4/1994 | Itoh et al. | 502/61 |
| 5,382,741 A | | 1/1995 | Astbury et al. | 585/652 |
| 5,436,383 A | | 7/1995 | Peltier et al. | 585/655 |
| 5,478,528 A | | 12/1995 | Golunski et al. | 482/88 |
| 5,527,979 A | | 6/1996 | Agaskar et al. | 585/654 |
| 5,593,935 A | | 1/1997 | Golunski et al. | 502/334 |
| 5,625,111 A | | 4/1997 | Astbury et al. | 585/653 |
| 5,633,421 A | | 5/1997 | Iezzi et al. | 585/660 |
| 5,639,929 A | | 6/1997 | Bharadwaj et al. | 585/658 |
| 5,648,582 A | | 7/1997 | Schmidt et al. | 585/652 |
| 5,654,491 A | | 8/1997 | Goetsch et al. | 568/464.4 |
| 5,658,497 A | | 8/1997 | Kumar et al. | 252/373 |
| 5,677,260 A | | 10/1997 | Dongara et al. | 502/334 |
| 5,817,596 A | | 10/1998 | Akporiaye et al. | 502/327 |
| 5,905,180 A | | 5/1999 | Yokoyama et al. | 585/658 |

FOREIGN PATENT DOCUMENTS

| | | |
|---|---|---|
| EP | 0178853 | 4/1986 |
| EP | 332289 | * 9/1989 |
| WO | WO 90/06282 | 6/1990 |

OTHER PUBLICATIONS

Hackh's Chemical Dictionary; p. 444, 1969.*
C. Yokoyama, S. S. Bharadwaj, and L. D. Schmidt, "Platinum–Tin and Platinum–Copper Catalysts for Autothermal Oxidative Dehydrogenation of Ethane to Ethylene," Catalysis Letters, 38 (1996), 181–188.
M. Huff and L. D. Schmidt, "Production of Olefins by Oxidative Dehydrogenation of Propane and Butane Over Monoliths at Short Contact Times," Journal of Catalysis, 149 (1994), 127–141.
M. Huff and L. D. Schmidt, "Ethylene Formation by Oxidative Dehydrogenation of Ethane over Monoliths at Very Short Contact Times," Journal of Physical Chemistry, 97 (1993), 11,815–11,822.

* cited by examiner

Primary Examiner—Thuan D. Dang

(57) ABSTRACT

A process and catalyst for the partial oxidation of paraffinic hydrocarbons, such as ethane, propane, naphtha, and natural gas condensates, to olefins, such as ethylene and propylene. The process involves contacting a paraffinic hydrocarbon with oxygen in the presence of hydrogen and a catalyst under autothermal process conditions. Preheating the feed decreases oxygen consumption and increases the net hydrogen balance. The catalyst comprises a Group 8B metal, preferably, a platinum group metal, and at least one promoter selected from Groups 1B, 6B, 3A, 4A, and 5A, optionally supported on a catalytic support, such as magnesia or alumina. In preferred embodiments, the support is pretreated with a support modifier selected from Groups 1A, 2A, 3B, 4B, 5B, 6B, 1B, 3A, 4A, 5A, the rare earth lanthanides, and the actinides. A modified fluidized bed reactor is disclosed for the process.

43 Claims, No Drawings

AUTOTHERMAL PROCESS FOR THE PRODUCTION OF OLEFINS

CROSS-REFERENCES TO RELATED APPLICATIONS

This application claims the benefit of U.S. Provisional Application Ser. No. 60/099,041, filed Sep. 3, 1998, U.S. Provisional Application Ser. No. 60/111,861, filed Dec. 11, 1998, and U.S. Provisional Application Ser. No. 60/136,003, filed May 26, 1999.

BACKGROUND OF THE INVENTION

The present invention relates to the field of catalytic oxidation of hydrocarbons. More particularly, the present invention relates to the catalytic partial oxidation of paraffinic hydrocarbons, such as ethane, propane, and naphtha, to produce olefins, such as ethylene and propylene.

Olefins find widespread utility in industrial organic chemistry. Ethylene is needed for the preparation of important polymers, such as polyethylene, vinyl plastics, and ethylene-propylene rubbers, and important basic chemicals, such as ethylene oxide, styrene, acetaldehyde, ethyl acetate, and dichloroethane. Propylene is needed for the preparation of polypropylene plastics, ethylene-propylene rubbers, and important basic chemicals, such as propylene oxide, cumene, and acrolein. Isobutylene is needed for the preparation of methyl tertiary butyl ether. Long chain mono-olefins find utility in the manufacture of linear alkylated benzene sulfonates, which are used in the detergent industry.

Low molecular weight olefins, such as ethylene, propylene, and butylene, are produced almost exclusively by thermal cracking (pyrolysis/steam cracking) of alkanes at elevated temperatures. An ethylene plant, for example, typically achieves an ethylene selectivity of about 85 percent calculated on a carbon atom basis at an ethane conversion of about 60 mole percent. Undesired coproducts are recycled on the shell side of the cracking furnace to be burned, so as to produce the heat necessary for the process. Disadvantageously, thermal cracking processes for olefin production are highly endothermic. Accordingly, these processes require the construction and maintenance of large, capital intensive, and complex cracking furnaces. The heat required to operate these furnaces at a process temperature of about 900° C. is frequently obtained from the combustion of methane which disadvantageously produces undesirable quantities of carbon dioxide. As a further disadvantage, the crackers must be shut down periodically to remove coke deposits on the inside of the cracking coils.

Catalytic processes are known wherein paraffinic hydrocarbons are oxidatively cracked to form mono-olefins. In these processes a paraffinic hydrocarbon is contacted with oxygen in the presence of a catalyst consisting of a platinum group metal or mixture thereof deposited on a ceramic monolith support. Optionally, hydrogen may be a component of the feed. The process is conducted under autothermal reaction conditions wherein the feed is partially combusted, and the heat produced during combustion drives the endothermic cracking process. Consequently, under these autothermal process conditions there is no external heat source required; however, the catalyst is required to support combustion above the normal fuel-rich limit of flammability. Representative references disclosing this type of process include the following U.S. Pat. Nos. 4,940,826; 5,105,052; 5,382,741; and 5,625,111. Disadvantageously, substantial amounts of deep oxidation products, such as carbon monoxide and carbon dioxide, are produced, and the selectivity to olefins remains too low when compared with thermal cracking.

M. Huff and L. D. Schmidt disclose in the *Journal of Physical Chemistry*, 97, 1993, 11,815, the production of ethylene from ethane in the presence of air or oxygen under autothermal conditions over alumina foam monoliths coated with platinum, rhodium, or palladium. A similar article by M. Huff and L. D. Schmidt in the *Journal of Catalysis*, 149, 1994, 127–141, discloses the autothermal production of olefins from propane and butane by oxidative dehydrogenation and cracking in air or oxygen over platinum and rhodium coated alumina foam monoliths. The olefin selectivity achieved in these processes is not comparable to that achieved by steam cracking and therefore could be improved.

U.S. Pat. No. 5,639,929 teaches an autothermal process for the oxidative dehydrogenation of $C_2$–$C_6$ alkanes with an oxygen-containing gas in a fluidized catalyst bed of platinum, rhodium, nickel, or platinum-gold supported on alpha alumina or zirconia. Ethane produces ethylene, while higher alkanes produce ethylene, propylene, and isobutylene. Again, the olefin selectivity could be improved.

C. Yokoyama, S. S. Bharadwaj and L. D. Schmidt disclose in *Catalysis Letters*, 38, 1996, 181–188, the oxidative dehydrogenation of ethane to ethylene under autothermal reaction conditions in the presence of a bimetallic catalyst comprising platinum and a second metal selected from tin, copper, silver, magnesium, cerium, lanthanum, nickel, cobalt, and gold supported on a ceramic foam monolith. This reference is silent with respect to co-feeding hydrogen in the feedstream. While the use of a catalyst containing platinum and tin and/or copper is better than a catalyst containing a platinum group metal alone, the olefin selectivity should be improved if the process is to be commercialized.

In view of the above, it would be desirable to discover a catalytic process wherein a paraffinic hydrocarbon is converted to an olefin in a conversion and selectivity comparable to commercial thermal cracking processes. It would be desirable if the catalytic process were to produce only small quantities of deep oxidation products, such as, carbon monoxide and carbon dioxide. It would also be desirable if the process were to achieve low levels of catalyst coking. It would be even more desirable if the process could be easily engineered without the necessity for a large, capital intensive, and complex cracking furnace. Finally, it would be most desirable if the catalyst for the process exhibited good stability.

SUMMARY OF THE INVENTION

This invention is a process for the partial oxidation of paraffinic hydrocarbons to form olefins. The process comprises contacting a paraffinic hydrocarbon or mixture thereof with oxygen in the presence of hydrogen and a catalyst. The contacting is conducted under autothermal process conditions sufficient to form the olefin. The catalyst employed in the process of this invention comprises a Group 8B metal and at least one promoter.

The process of this invention efficiently produces olefins, particularly mono-olefins, from paraffinic hydrocarbons, oxygen, and hydrogen. Advantageously, the process of this invention achieves a higher paraffin conversion and a higher olefin selectivity as compared with prior art catalytic, autothermal processes. More advantageously, the process of this invention produces fewer undesirable deep oxidation products, such as carbon monoxide and carbon dioxide, as compared with prior art catalytic, autothermal processes. Even more advantageously, in preferred embodiments, the process of this invention achieves a paraffin conversion and olefin selectivity which are comparable to commercial thermal cracking processes. As a further advantage, the process produces little, if any, coke, thereby substantially prolonging catalyst lifetime and eliminating the necessity to shut down the reactor to remove coke deposits.

Most advantageously, the process of this invention allows the operator to employ a simple engineering design and control strategy, which eliminates the requirement for a large, expensive, and complex furnace like that used in thermal cracking processes. In one preferred embodiment, the reactor simply comprises an exterior housing which contains a monolithic support onto which the catalytic components are deposited. Since the residence time of the reactants in the process of this invention is on the order of milliseconds, the reaction zone operates at high volumetric throughput. Accordingly, the reaction zone measures from about one-fiftieth to about one-hundredth the size of a commercially available steam cracker of comparable capacity. The reduced size of the reactor lowers costs and simplifies maintenance procedures. Finally, since the process of this invention is exothermic, the heat produced can be harvested via integrated heat exchangers to generate electricity or steam credits for other processes.

As noted hereinbefore, thermal energy is needed to maintain autothermal process conditions. Without preheating the feedstream, the required thermal energy is totally supplied by the reaction of the feedstream with oxygen, namely, alkane oxidative dehydrogenation to form olefins and water, hydrogen oxidation to form water, and carbon combustion to form carbon monoxide and carbon dioxide. These processes can supply the heat necessary for any endothermic dehydrogenation which takes place to form ethylene and hydrogen. The prior art has recognized that a portion of the required thermal energy can be obtained by preheating the feedstream. The preheat can be conveniently supplied by condensing high pressure saturated steam, or alternatively, by combusting process off-gas or another fuel source. Surprisingly, it has now been discovered that a high preheat temperature can be used without loss in olefin selectivity, and further, that a high preheat temperature provides advantages unrecognized heretofore. Accordingly, in another aspect of this invention, the paraffinic hydrocarbon and oxygen, which together comprise the reactant feedstream, are preheated at a temperature greater than about 200° C., but below the onset of reaction of the feedstream components.

When the high preheat temperatures of this invention are employed, advantageously less oxygen is required in the feedstream. Since the cost of pure oxygen can be a significant cost component of the feedstream, the decrease in oxygen employed translates directly into economic savings. Moreover, since oxygen reacts with hydrogen in the feedstream, the decrease in oxygen employed leads to a decrease in hydrogen consumed and in the waste water produced. As a consequence, more hydrogen is found in the product stream.

An increased yield of hydrogen in the product stream further improves the economics of the autothermal oxidation process of this invention. Since hydrogen is required for the process, hydrogen in the product should be recycled and any deficit must be replaced by importing hydrogen from an external source. Alternatively, hydrogen can be made from off-gas streams, for example, a water-shift reaction which converts carbon monoxide and water to hydrogen and carbon dioxide. As a consequence of using the high preheat temperature of this invention, the product stream is enriched in hydrogen. Under optimal preheat conditions, the recycled hydrogen substantially eliminates the need to import hydrogen or to derive make-up hydrogen from other sources.

In a third aspect, the autothermal oxidation process of this invention is beneficially conducted in a unique fluidized bed reactor, characterized in that the reactor bed possesses an aspect ratio of less than about 1:1, as measured during operation. For the purposes of this invention, the aspect ratio is defined as the ratio of the height (or depth) of the reactor bed to its cross-sectional dimension (diameter or width). For use in this fluidized bed, the catalyst comprises a support in the form of pellets or spheres onto which the catalytic components are deposited.

When operation of the process in the aforementioned unique fluidized bed reactor is compared with operation in a fixed bed reactor, several advantages become apparent. For example, ethylene selectivity improves with use of the fluidized bed, while selectivities to methane and deep oxidation products, such as carbon monoxide and carbon dioxide, decrease. Significantly, the selectivity advantages are achieved at ethane conversions which are comparable to or better than those obtained in a fixed bed reactor.

In a fourth aspect, this invention is a catalyst composition comprising a Group 8B metal and at least one promoter supported on a catalyst support which has been pretreated with at least one support modifier.

The aforementioned composition is beneficially employed as a catalyst in the autothermal partial oxidation of a paraffinic hydrocarbon to an olefin. The catalyst composition beneficially produces an olefin or mixture of olefins at conversions and selectivities which are comparable to those of industrial thermal cracking processes. Accordingly, the catalyst composition of this invention produces low amounts of carbon monoxide and carbon dioxide. Finally, the catalyst composition of this invention advantageously exhibits good catalyst stability.

DETAILED DESCRIPTION OF THE INVENTION

The process of this invention involves the partial oxidation of a paraffinic hydrocarbon to form an olefin. The words "partial oxidation" imply that the paraffin is not substantially oxidized to deep oxidation products, specifically, carbon monoxide and carbon dioxide. Rather, the partial oxidation comprises one or both of oxidative dehydrogenation and cracking to form primarily olefins. It is not known or suggested to what extent or degree either process, oxidative dehydrogenation or cracking, predominates or occurs to the exclusion of the other.

The partial oxidation process of this invention comprises contacting a paraffinic hydrocarbon with oxygen in the presence of a multi-metallic catalyst and in the presence of a hydrogen co-feed. The contacting is conducted under autothermal process conditions sufficient to form the olefin. The catalyst which is employed in the process of this invention comprises a Group 8B metal and at least one promoter, optionally supported on a catalyst support. In a preferred embodiment of the process of this invention, the paraffinic hydrocarbon is a paraffin selected from ethane, propane, mixtures of ethane and propane, naphtha, natural gas condensates, and mixtures of the aforementioned hydrocarbons; and the preferred olefins produced are ethylene, propylene, butylene, isobutylene, and butadiene.

In a preferred aspect of this invention, the feedstream comprising the paraffinic hydrocarbon and oxygen is preheated before introducing the feedstream into the autothermal oxidation reactor. The preheat temperature is greater than about 200° C., but less than the temperature wherein reaction of the feedstream components begins. Preferably, the upper limit on the preheat temperature is less than about 900° C.

In another preferred embodiment of this invention, the reactor comprises an exterior housing which holds the catalyst, the catalyst being provided in the form of a ceramic monolith support onto which the catalytic components, including the Group 8B metal and any promoter(s), have been deposited.

In another preferred aspect of this invention, the reactor comprises a modified fluidized bed characterized by an aspect ratio of less than about 1:1 in operating mode. As noted hereinbefore, the aspect ratio is the ratio of the height (depth) of the reactor to its cross-sectional dimension (diameter or width). In this reactor, the catalyst is provided typically in the form of spheres or granules.

In yet another preferred embodiment, the catalyst which is employed in the process of this invention comprises a Group 8B metal and at least one promoter supported on a catalytic support which has been pretreated with at least one support modifier. Preferably, the Group 8B metal is a platinum group metal. The preferred platinum group metal is platinum. The preferred promoter is selected from the elements of Groups 1B, 6B, 3A, 4A, 5A, (equivalent to Groups 11, 6, 13, 14, and 15), and mixtures of the aforementioned elements of the Periodic Table, as referenced by S. R. Radel and M. H. Navidi, in Chemistry, West Publishing Company, New York, 1990. The preferred support modifier is selected from Groups 1A, 2A, 3B, 4B, 5B, 6B, 1B, 3A, 4A, 5A (equivalent Groups 1, 2, 3, 4, 5, 6, 11, 13, 14, 15), and the lanthanide rare earths and actinide metals of the Periodic Table, as referenced by S. R. Radel and M. H. Navidi, ibid.

In a most preferred embodiment of the catalyst composition, the platinum group metal is platinum; the promoter is selected from tin, copper, and mixtures thereof; the support is selected from alumina, magnesia, and mixtures thereof; and the modifier is selected from tin, lanthanum, and mixtures thereof.

Any paraffinic hydrocarbon or mixture of paraffinic hydrocarbons can be employed in the process of this invention provided that an olefin, preferably, a mono-olefin, is produced. The term "paraffinic hydrocarbon," as used herein, refers to a saturated hydrocarbon. Generally, the paraffin contains at least 2 carbon atoms. Preferably, the paraffin contains from 2 to about 25 carbon atoms, more preferably, from 2 to about 15 carbon atoms, and even more preferably, from 2 to about 10 carbon atoms. The paraffin can have a linear, branched, or cyclic structure, and can be a liquid or gas at ambient temperature and pressure. The paraffin can be supplied as an essentially pure paraffinic compound, or mixture of paraffinic compounds, or as a paraffin-containing mixture of hydrocarbons. Paraffin feeds which are suitably employed in the process of this invention include, but are not limited to, ethane, propane, butane, pentane, hexane, heptane octane, and higher homologues thereof, as well as complex higher boiling mixtures of paraffin-containing hydrocarbons, such as naphtha, gas oil, vacuum gas oil, and natural gas condensates. Additional feed components may include methane, nitrogen, carbon monoxide, carbon dioxide, and steam, if so desired. Minor amounts of unsaturated hydrocarbons may also be present. Most preferably, the paraffin is selected from ethane, propane, mixtures of ethane and propane, naphtha, natural gas condensates, and mixtures thereof.

In the process of this invention, the paraffinic hydrocarbon is contacted with an oxygen-containing gas. Preferably, the gas is molecular oxygen or molecular oxygen diluted with an unreactive gas, such as nitrogen, helium, carbon dioxide, or argon, or diluted with a substantially unreactive gas, such as carbon monoxide or steam. Any molar ratio of paraffin to oxygen is suitable provided the desired olefin is produced in the process of this invention. Preferably, the process is conducted fuel-rich and above the upper flammability limit. Generally, the molar ratio of paraffinic hydrocarbon to oxygen varies depending upon the specific paraffin feed and autothermal process conditions employed. Typically, the molar ratio of paraffinic hydrocarbon to oxygen ranges from about 3 to about 77 times the stoichiometric ratio of hydrocarbon to oxygen for complete combustion to carbon dioxide and water. Preferably, the molar ratio of paraffinic hydrocarbon to oxygen ranges from about 3 to about 13, more preferably, from about 4 to about 11, and most preferably, from about 5 to about 9 times the stoichiometric ratio of hydrocarbon to oxygen for complete combustion to carbon dioxide and water. These general limits are usually achieved by employing a molar ratio of paraffinic hydrocarbon to oxygen greater than about 0.1:1, preferably, greater than about 0.2:1, and by using a molar ratio of paraffinic hydrocarbon to oxygen usually less than about 3.0:1, preferably, less than about 2.7:1. For preferred paraffins, the following ratios are more specific. For ethane, the ethane to oxygen molar ratio is typically greater than about 1.5:1, and preferably, greater than about 1.8:1. The ethane to oxygen molar ratio is typically less than about 3.0:1, preferably, less than about 2.7:1. For propane, the propane to oxygen molar ratio is typically greater than about 0.9:1, preferably, greater than about 1.1:1. The propane to oxygen molar ratio is typically less than about 2.2:1, preferably, less than about 2.0:1. For naphtha, the naphtha to oxygen molar ratio is typically greater than about 0.3:1, preferably, greater than about 0.5:1. The naphtha to oxygen molar ratio is typically less than about 1.0:1, preferably, less than about 0.9:1.

When a high preheat temperature is used, for example, above 200° C., the limits on the molar ratio of paraffinic hydrocarbon to oxygen can be shifted towards higher values. For example, at high preheat the molar ratio of paraffinic hydrocarbon to oxygen is typically greater than about 0.1:1 and less than about 4.0:1. Specifically, at high preheat the ethane to oxygen molar ratio is typically greater than about 1.5:1, preferably, greater than about 1.8:1, and typically less than about 4.0:1, preferably, less than about 3.2:1. At high preheat, the molar ratio of propane to oxygen is typically greater than about 0.9:1, preferably, greater than about 1.1:1, and typically, less than about 3.0:1, and preferably, less than about 2.6:1. At high preheat, the molar ratio of naphtha to oxygen is typically greater than about 0.3:1, preferably, greater than about 0.5:1, and typically, less than about 1.4:1, and preferably, less than about 1.3:1. As an advantageous feature of the process of this invention, hydrogen is co-fed with the paraffin and oxygen to the catalyst. The presence of hydrogen in the feedstream beneficially improves the conversion of hydrocarbon and the selectivity to olefins, while reducing the formation of deep oxidation products, such as, carbon monoxide and carbon dioxide. The molar ratio of hydrogen to oxygen can vary over any operable range provided that the desired olefin product is produced. Typically, the molar ratio of hydrogen to oxygen is greater than about 0.5:1, preferably, greater than about 0.7:1, and more preferably, greater than about 1.5:1. Typically, the molar ratio of hydrogen to oxygen is less than about 3.2:1, preferably, less than about 3.0:1, and more preferably, less than about 2.7:1.

At high preheat the molar ratio of hydrogen to oxygen typically is greater than about 0.1:1, preferably, greater than about 0.7:1, and more preferably, greater than about 1.5:1. At high preheat the molar ratio of hydrogen to oxygen is typically less than about 4.0:1, preferably, less than about 3.2:1, and more preferably, less than about 3.0:1.

Optionally, the feed may contain a diluent, which can be any gas or vaporizable liquid which does not interfere with the process of the invention. The diluent functions as a carrier of the reactants and products and facilitates the transfer of heat generated by the process. The diluent also helps to minimize undesirable secondary reactions and helps to expand the non-flammable regime for mixtures of the paraffin, hydrogen, and oxygen. Suitable diluents include nitrogen, argon, helium, carbon dioxide, carbon monoxide, methane, and steam. The concentration of diluent in the feed can vary over a wide range. If a diluent is used, the concentration of diluent is typically greater than about 0.1 mole percent of the total reactant feed including paraffin, oxygen, hydrogen, and diluent. Preferably, the amount of diluent is greater than about 1 mole percent of the total reactant feed. Typically, the amount of diluent is less than about 70 mole percent, and preferably, less than about 40 mole percent, of the total reactant feed.

The catalyst which is employed in the process of this invention beneficially comprises a Group 8B metal and at least one promoter, described hereinbelow, optionally supported on a catalyst support. The Group 8B metals include iron, cobalt, nickel, and the platinum group metals, namely, ruthenium, rhodium, palladium, osmium, iridium, and platinum. Mixtures of the aforementioned Group 8B metals may also be used. Preferably, the Group 8B metal is a platinum group metal; preferably, the platinum group metal is platinum. The catalyst also comprises at least one promoter, which is suitably defined as any element or elemental ion which is capable of enhancing the performance of the catalyst, as measured, for example, by an increase in the paraffin conversion, an increase in the selectivity to olefin, a decrease in the selectivities to deep oxidation products, such as carbon monoxide and carbon dioxide, and/or an increase in catalyst stability and lifetime. For the purposes of this invention, the term "promoter" does not include t group metals. Preferably, the promoter is selected from the elements of Groups 1B (Cu, Ag, Au), 6B (Cr, Mo, W), 3A (for example, Al, Ga, In, Tl), 4A (for example, Ge, Sn, Pb), and 5A (for example, As, Sb, Bi), and mixtures thereof. More preferably, the promoter is selected from copper, tin, antimony, silver, indium, and mixtures thereof. Most preferably, the promoter is selected from copper, tin, antimony, and mixtures thereof.

Any atomic ratio of Group 8B metal to promoter can be employed in the catalyst, provided the catalyst is operable in the process of this invention. The optimal atomic ratio will vary with the specific Group 8B metal and promoter(s) employed. Generally, the atomic ratio of the Group 8B metal to promoter is greater than 0.10 (1:10), preferably, greater than about 0.13 (1:8), and more preferably, greater than about 0.17 (1:6). Generally, the atomic ratio of the Group 8B metal to promoter is less than about 2.0 (1:0.5), preferably, less than about 0.33 (1:3), and more preferably, less than about 0.25 (1:4). Although the promoter is used in a gramatom amount equivalent to or greater than the Group 8B metal, the promoter nonetheless functions to enhance the catalytic effect of the catalyst. Compositions prepared with promoter alone, in the absence of Group 8B metal, are typically (but not necessarily always) catalytically inactive in the process. In contrast, the Group 8B metal is catalytically active in the absence of promoter, albeit with lesser activity.

The catalyst can be suitably employed in the form of a metallic gauze. More specifically, the gauze can comprise an essentially pure Group 8B metal or an alloy of Group 8B metals onto which the promoter is deposited. Suitable gauzes of this type include pure platinum gauze and platinum-rhodium alloy gauze coated with the promoter. The method used to deposit or coat the promoter onto the gauze can be any of the methods described hereinafter. Alternatively, a gauze comprising an alloy of a Group 8B metal and the promoter can be employed. Suitable examples of this type include gauzes prepared from platinum-tin, platinum-copper, and platinum-tin-copper alloys.

In another embodiment, the Group 8B metal and promoter are supported on a catalytic support. The loading of the Group 8B metal on the support can be any which provides for an operable catalyst in the process of this invention. In general, the loading of the Group 8B metal is greater than about 0.001 weight percent, preferably, greater than about 0.1 weight percent, and more preferably, greater than about 0.2 weight percent, based on the total weight of the Group 8B metal and support. Preferably, the loading of the Group 8B metal is less than about 80 weight percent, preferably, less than about 60 weight percent, and more preferably, less than about 10 weight percent, based on the total weight of the Group 8B metal and the support. Once the Group 8B metal loading is established, the desired atomic ratio of Group 8B metal to promoter determines the loading of the promoter.

The catalytic support comprises any material which provides a surface to carry the Group 8B metal, the promoter(s), and any support modifiers. Preferably, the support is thermally and mechanically stable under autothermal process conditions. Preferably, the catalytic support is a ceramic, such as, a refractory oxide, carbide, or nitride. Non-limiting examples of suitable ceramics include alumina, silica, silica-aluminas, aluminosilicates, including cordierite, magnesia, magnesium aluminate spinels, magnesium silicates, zirconia, titania, boria, zirconia toughened alumina (ZTA), lithium aluminum silicates, silicon carbide, oxide-bonded silicon carbide, and silicon nitride. Mixtures of the aforementioned refractory oxides, nitrides, and carbides may also be employed, as well as washcoats of the aforementioned materials on a support. Preferred ceramics include magnesia, alumina, silica, and amorphous or crystalline combinations of magnesia, alumina and silica, including mullite. Alpha ($\alpha$) and gamma ($\gamma$) alumina are preferred forms of alumina. Preferred combinations of alumina and silica comprise from about 65 to about 100 weight percent alumina and from essentially 0 to about 35 weight percent silica. Other refractory oxides, such as boria, can be present in smaller amounts in the preferred alumina and silica mixtures. Preferred zirconias include zirconia fully stabilized with calcia (FSZ) and zirconia partially stabilized with magnesia (PSZ), available from Vesuvius Hi-Tech Ceramics, Inc. Magnesia is the most preferred support, because it produces fewer cracking products and less carbon monoxide. Moreover, the hydrocarbon conversion and olefin selectivity tend to be higher with magnesia. The catalytic support may take a variety of shapes including that of porous or non-porous spheres, granules, pellets, irregularly shaped solid or porous particles, or any other shape which is suitable for catalytic reactors, including fixed bed, transport bed, and fluidized bed reactors. In a preferred form, the catalyst is a monolith. As used herein, the term "monolith" means any continuous structure, including for example, honeycomb structures, foams, and fibers, including fibers woven into fabrics or made into non-woven mats or thin paper-like sheets. Monoliths do not, in general, contain significant microporosity. Foams have a sponge-like structure. More preferably, the support is a foam or fiber monolith. Fibers tend to possess higher fracture resistance as compared with foams and honeycombs. Preferred ceramic foams, available from Vesuvius Hi-Tech Ceramics, Inc., comprise magnesia, alpha alumina, zirconia, or mullite with a porosity ranging from about 5 to about 100 pores per linear inch (ppi) (2 to 40 pores per linear cm (ppcm)). Foams having about 45 ppi (18 ppcm) are more preferred. The term "porosity," as used herein, refers to channel size or dimension. It is important to note that the foam supports are not substantially microporous structures. Rather, the foams are macroporous, meaning that they are low surface area supports with channels ranging in diameter from about 0.1 mm to about 5 mm. The foams are estimated to have a surface area less than about 10 $m^2/g$, and preferably, less than about 2 $m^2/g$, but greater than about 0.001 $m^2/g$. Preferred ceramic fibers available from 3M Corporation as Nextel™ brand ceramic fibers, typically have a diameter greater than about 1 micron ($\mu$m), preferably, greater than about 5 $\mu$m. The diameter is suitably less than about 20 $\mu$m, preferably, less than about 15 $\mu$m. The length of the fibers is generally greater than about 0.5 inch (1.25 cm), preferably, greater than about 1 inch (2.5 cm), and typically less than about 10 inches (25.0 cm), preferably, less than about 5 inches (12.5 cm). The surface area of the fibers is very low, being generally less than about 1 $m^2/g$, preferably, less than about 0.3 $m^2/g$, but greater than about 0.001 $m^2/g$. Preferably, the fibers are not woven like cloth, but instead are randomly intertwined as in a mat or matted rug. Most preferred are Nextel™ brand 440 fibers which consist of gamma alumina (70 weight percent), silica (28 weight percent), and boria (2 weight percent) and Nextel™ brand 610 fibers which consist of alpha alumina (99 weight percent), silica (0.2–0.3 weight percent) and iron oxide (0.4–0.7 weight percent).

The deposition of the Group 8B metal and promoter(s) onto the support can be made by any technique known to those skilled in the art, for example, impregnation, ion-exchange, deposition-precipitation, vapor deposition, sputtering, and ion implantation. In one preferred methods the Group 8B metal is deposited onto the support by impregnation. Impregnation is described by Charles N. Satterfield in *Heterogeneous Catalysis in Practice*, McGraw-Hill Book Company, New York, 1980, 82–84, incorporated herein by reference. In this procedure, the support is wetted with a solution containing a soluble Group 8B compound, preferably, to the point of incipient wetness. The contacting temperature typically ranges from about ambient, taken as 23° C., to about 100° C., preferably, from about 23° C. to about 50° C. The contacting is conducted usually at ambient pressure. Non-limiting examples of suitable Group 8B compounds include the Group 8B nitrates, halides, sulfates, alkoxides, carboxylates, and Group 8B organometallic compounds, such as halo, amino, acetylacetonate, and carbonyl complexes. Preferably, the Group 8B compound is a platinum group halide, more preferably, a chloride, such as chloroplatinic acid. The solvent can be any liquid which solubilizes the Group 8B compound. Suitable solvents include water, aliphatic alcohols, aliphatic and aromatic hydrocarbons, and halo-substituted aliphatic and aromatic hydrocarbons. The concentration of the Group 8B compound in the solution generally ranges from about 0.001 molar (M) to about 10 M. After contacting the support with the solution containing the Group 8B compound, the support may be dried under air at a temperature ranging from about 23° C. to a temperature below the decomposition temperature of the Group 8B compound, typically, a temperature between about 23° C. and about 100° C.

The deposition of the promoter can be accomplished in a manner analogous to the deposition of the Group 8B metal. Accordingly, if impregnation is used, then the support is wetted with a solution containing a soluble compound of the promoter at a temperature between about 23° C. and about 100° C., preferably, between about 23° C. and about 50° C., at about ambient pressure. Suitable examples of soluble promoter compounds include promoter halides, nitrates, alkoxides, carboxylates, sulfates, and organometallic compounds, such as amino, halo, and carbonyl complexes. Suitable solvents comprise water, aliphatic alcohols, aliphatic and aromatic hydrocarbons, and chloro-substituted aliphatic and aromatic hydrocarbons. Certain promoter compounds, such as compounds of antimony and tin, may be more readily solubilized in the presence of acid. For example, hydrochloric acid (5–25 weight percent) can be suitably employed. The concentration of the promoter compound in the solution generally ranges from about 0.01 M to about 10 M. Following deposition of the soluble promoter compound or mixture thereof, the impregnated support may be dried under air at a temperature between about 23° C. and a temperature below the temperature wherein vaporization or decomposition of the promoter compound occurs. Typically, the drying is conducted at a temperature between about 23° C. and about 100° C.

In one method of preparing the catalyst, the Group 8B metal is deposited onto the support first, and thereafter the promoter is deposited onto the support. In an alternative method, the promoter is deposited first, followed by the deposition of the Group 8B metal. In a preferred method of preparing the catalyst, the Group 8B metal and the promoter are deposited simultaneously onto the support from the same deposition solution. In any of these methods, following one or more of the depositions, a calcination under oxygen is optional. If performed, the calcination is conducted at a temperature ranging from about 100° C. to below the temperature at which volatilization of the metals becomes significant, typically, less than about 1,100° C. Preferably, the calcination is conducted at a temperature between about 100° C. and about 500° C.

As a final step in the preparation of the catalyst, the fully-loaded support is reduced under a reducing agent, such as hydrogen, carbon monoxide, or ammonia, at a temperature between about 100° C. and about 900° C., preferably between about 125° C. and about 800° C., so as to convert the Group 8B metal substantially to its elemental form. The promoter may be reduced fully or partially, or not reduced at all, depending upon the specific promoter chosen and the reduction conditions. In addition, reduction at elevated temperatures may produce alloys of the Group 8B metal and the promoter. Alloys may provide enhanced catalyst stability by retarding vaporization of the promoter during the process of this invention.

In another preferred embodiment, the support is pretreated with a support modifier prior to loading the Group 8B and promoter(s). The support modifier can be any metal ion having a charge of +1 or greater. Preferably, the support modifier is selected from Groups 1A (Li, Na, K, Rb, Cs), 2A (for example, Mg, Ca, Sr, Ba), 3B (Sc, Y, La), 4B (Ti, Zr, Hf), 5B (V, Nb, Ta), 6B (Cr, Mo, W), 1B (Cu, Ag, Au), 3A (for example, Al, Ga, In), 4A (for example, Ge, Sn, Pb), 5A (for example, As, Sb, Bi), and the lanthanide rare earths (for example, Ce, Er, Lu, Ho) and actinide elements (specifically Th) of the Periodic Table previously identified. More preferably, the support modifier is selected from calcium, zirconium, tin, lanthanum, potassium, lutetium, erbium, barium, holmium, cerium, antimony, and mixtures thereof. Most preferably, the support modifier is selected from lanthanum, tin, antimony, calcium, and mixtures thereof. Certain elements, such as tin, antimony, and silver, may function as both promoter and support modifier simultaneously.

The procedure to modify the support comprises contacting the support with a solution containing a soluble compound of the support modifier. The contacting can involve ion-exchange or impregnation methods. Preferably, the modification procedure involves submerging the support in the solution such that essentially all of the surface area of the support is contacted with an excess of the solution. Compounds suitable for preparing the solution of support modifier include modifier nitrates, halides, particularly the chlorides, alkoxides, carboxylates, and organometallic complexes including amino, halo, alkyl, and carbonyl complexes. Suitable solvents include water, aliphatic alcohols, aromatic hydrocarbons, and halo-substituted aliphatic and aromatic hydrocarbons. Typically, the concentration of modifier compound in the solution ranges from about 0.001 M to about 10 M. Acidified solutions, for example, of hydrochloric acid and diluted solutions thereof, may be beneficially employed. The contact time generally ranges from about 1 minute to about 1 day. The contacting temperature suitably ranges from about 23° C. to about 100° C., and pressure is generally ambient. Alternatively, slurries of mixed oxides containing promoter and/or modifier elements, such as magnesium stannate ($Mg_2SnO_4$), can be deposited onto the support; The modified support is typically calcined, as noted hereinabove, or reduced under a reducing agent, such as hydrogen, at a temperature between about 100° C. and about 900° C., preferably, between about 200° C. and about 800° C. The choice of calcination or reduction depends on the element used to pretreat the support. If the element or its oxide is readily vaporizable, the pretreated support is reduced. If the element or its oxide is not readily vaporizable, then the pretreated support is calcined. As a guideline, the words "readily vaporizable" may be taken to mean that greater than about 1 weight percent of any metal component in the catalyst is vaporized in a period of about 24 hours under calcination conditions at about 200° C. The term "readily vaporizable" may be given a narrower or broader definition, as desired.

Following the pretreatment modification, the Group 8B metal and promoter(s) are loaded onto the support. Then, the support is reduced as described hereinbefore Alternatively, the metal-loaded support may be calcined first and then reduced. Whether the modified support is calcined or not depends again upon the vaporization potential of the modifier metal(s) and promoter(s) employed. Supports modified with metals or metal oxides which tend to vaporize readily are typically not calcined. Support modified with metals or metal oxides which do not vaporize readily can be calcined.

The process of this invention is advantageously conducted under autothermal process conditions. The term "autothermal process conditions" means that the heat generated by reaction of the feed is sufficient to support the catalytic process which converts the paraffin to the olefin. Accordingly, the need for an external heating source to supply the energy for the process can be eliminated. In order to maintain autothermal conditions, the catalysts of the prior art are required to support combustion beyond the normal, fuel-rich limit of flammability. This is not a requirement in the present invention. Here, autothermal conditions can also be maintained with a catalyst which does not support combustion beyond the normal, fuel-rich limit of flammability, provided that hydrogen and optionally a preheat are supplied to the process.

Ignition can be effected by preheating the feed to a temperature sufficient to effect ignition when contacted with the catalyst. Alternatively, the feed can be ignited with an ignition source, such as a spark or flame. Upon ignition, the reaction-generated heat causes the temperature to take a step change jump to a new steady state level that is herein referred to as the autothermal reaction.

While running autothermal, the paraffin feed does not have to be preheated, so long as the feed contains hydrogen or the catalyst supports combustion beyond the normal, fuel-rich limit of flammability. (The word "combustion," as used herein, means the reaction of the hydrocarbon with oxygen unaided by hydrogen.) Preheating the feedstream, however, has certain advantages. The advantages comprise a decrease in oxygen and hydrogen consumed, an increase in the paraffin concentration in the feed, an increase in the operating paraffin to oxygen molar ratio, and a net increase in recycle hydrogen in the product cream. In addition, catalysts can be used which do not support combustion beyond the normal fuel-rich limit of flammability. These advantages are particularly significant when the preheating is conducted at a temperature greater than about 200° C. and less than the temperature wherein reaction of the feedstream components begins. Suitable preheat temperatures are typically greater than about 40° C., preferably, greater than about 125° C., and even more preferably, greater than about 200° C. In another preferred embodiment, the preheat temperature is greater than about 400° C. Suitable preheat temperatures are typically less than about 900° C., preferably, less than about 800° C., and more preferably less than about 600° C.

As a general rule, the autothermal process operates at close to the adiabatic temperature (that is, essentially without loss of heat), which is typically greater than about 75° C., and preferably, greater than about 925° C. Typically, the autothermal process operates at a temperature less than about 1,150° C., and preferably, less than about 1,050° C. Optionally, the temperature at the reactor exit can be measured, for example, by using a Pt/Pt—Rh thin wire thermocouple. With a monolith catalyst, the thermocouple can be sandwiched between the monolith and the downstream radiation shield. Measurement of temperature close to the reactor exit may be complicated by the high temperature involved and the fragility of the thermocouple. Thus, as an alternative, one skilled in the art can calculate the adiabatic temperature at the reactor exit from a knowledge of the preheat temperature and the exit stream composition. The "adiabatic temperature" is the temperature of the product stream without any heat loss, that is, when all of the heat generated by the process is used to heat the products. Typically, the measured temperature is found to be within about 25° C. of the calculated adiabatic temperature.

The operating pressure is typically equal to or greater than about 1 atmosphere absolute (atm abs) (100 kPa abs). Typically, the pressure is less than about 20 atm abs (2,000 kPa abs), preferably, less than about 10 atm (1,000 kPa abs), and more preferably, less than about 7 atm abs (700 kPa abs).

Since the products of this process must be removed rapidly from the reaction zone, gas hourly space velocities are very high. The specific gas hourly space velocity employed will depend upon the choice of reactor cross sectional dimension (for example, diameter) and the form and weight of the catalyst particles. Generally, the gas hourly space velocity (GHSV), calculated as the total flow of the hydrocarbon, oxygen, hydrogen, and optional diluent flows, is greater than about 50,000 ml total feed per ml catalyst per hour ($h^{-1}$) measured at standard temperature and pressure (0° C., 1 atm) (STP). Preferably, the GHSV is greater than about 80,000 $h^{-1}$, and more preferably, greater than 100,000 $h^{-1}$. Generally, the gas hourly space velocity is less than about 6,000,000 $h^{-1}$, preferably, less than about 4,000,000 $h^{-1}$, more preferably, less than 3,000,000 $h^{-1}$, measured as the total flow at STP. Gas flows are typically monitored in units of liters per minute at standard temperature and pressure (slpm). The conversion gas flow from "slpm" units to gas hourly s' pace velocity units ($h^{-1}$) is made as follows:

$$\text{GHSV } h^{-1} = \frac{\text{slpm} \times 1000 \text{ cm}^3/\text{min} \times 60 \text{ min/h}}{\text{cross-sectional area of catalyst (cm}^2) \times \text{length (cm)}}$$

The residence time of the reactants in the reactor is simply calculated as the inverse of the gas hourly space velocity. At the high space velocities employed in the process of this invention, the residence time is on the order of milliseconds. Thus, for example, a gas hourly space velocity of 100,000 $h^{-1}$ measured at STP is equivalent to a residence time of 36 milliseconds at STP.

The process of this invention may be conducted in any reactor designed for use under adiabatic, autothermal process conditions. In one preferred design, the catalyst is prepared on a monolith support which is sandwiched between two radiation shields inside a reactor housing. Alternatively, fixed bed and fluidized bed reactors can be used with catalysts in the form of pellets, spheres, and other particulate shapes. Continuous and intermittent flow of the feedstream are both suitable. It is noted that fluidized bed reactors of the prior art typically possess an aspect ratio in static mode of greater than 1:1, and more preferably, greater than about 5:1. Static mode is defined as the unfluidized or fixed bed configuration. Fluidized bed reactors are generally operated in a bubbling, turbulent, or fast-fluidized regime with expanded beds measuring from about 1.5 to 15 times the static depth. Typically, the aspect ratio in operating mode is greater than about 5:1 to 10:1. For full fluidization, a catalyst particle size ranging between about 30 and 1,000 microns is satisfactory.

It is believed that the oxidation reaction of this invention occurs predominantly at the reactor entry, which in the case of a stationary catalyst is at the front edge of the catalyst. Such a theory should not be binding or limiting of the invention in any manner. In view of this theory, the optimal reactor for the process of this invention should possess a large cross-sectional dimension and a short height (or depth). On a commercial scale, for example, a catalyst bed of diameter about 5 to 8 feet (1.5 m to 2.4 m) and a height of about 1 inch (2.5 cm) may be suitably employed. Additionally, it is believed that catalyst located at the front edge of a stationary bed can deactivate more quickly with time. As a consequence, longer catalyst lifetime and better selectivities can be achieved by circulating particles of the catalyst, rather than using a stationary bed.

A preferred reactor design for the process of this invention comprises a modified fluidized bed reactor, characterized in that its aspect ratio in operating mode, and preferably also in static mode (unfluidized or fixed bed configuration), is less than 1:1, and more preferably, less than about 0.1:1, but greater than about 0.001:1. Most preferably, the aspect ratio is about 0.01:1. This unique fluidized bed is operated above the minimum fluidization flow with an expanded bed on the order of about 2 or 3 times the static depth, and preferably, less than about 1.5 times the static depth. For the purposes of this invention, "minimum fluidization flow" is defined as the minimum gas velocity at which the catalyst particles are suspended under operating conditions. The velocity necessary to achieve minimum fluidization depends upon the density and viscosity of the gas phase and the catalyst particle size and density. One skilled in the art would know how to calculate the minimum fluidization flow for any given gas composition and catalyst particle. A suitable authority on the subject is found in *Fluidization Engineering*, by D. Kunii and O. Levenspeil, $2^{nd}$ ed., Butterworth-Heineman, 1989, incorporated herein by reference. A catalyst particle size of between about 500 and about 850 microns (23–30 US mesh) is suitable for feed velocities of about 0.05 to 5 meters per second (mps) at standard temperature and pressure. An advantage of the modified fluidized bed reactor may result from its continuous circulation (fluidization), which results in continuous renewal of catalyst particles at the reactor entry. This configuration produces substantially better product yields than a stationary catalyst.

When a paraffinic hydrocarbon is contacted with oxygen under autothermal process conditions in the presence of a co-feed of hydrogen and in the presence of the multi-metallic catalyst described hereinabove, an olefin, preferably a mono-olefin, is produced. Ethane is converted primarily to ethylene. Propane and butane are converted primarily to ethylene and propylene. Isobutane is converted primarily to isobutylene and propylene. Naphtha and other higher molecular weight paraffins are converted primarily to ethylene and propylene.

The conversion of paraffinic hydrocarbon in the process of this invention can vary depending upon the specific feed composition, catalyst composition, reactor, and process conditions employed. For the purposes of this invention, "conversion" is defined as the mole percentage of paraffinic hydrocarbon in the feed which is converted to products. Generally, at constant pressure and space velocity, the conversion increases with increasing temperature. Typically, at constant temperature and pressure, the conversion does not change significantly over a wide range of high space velocities employed. In this process, the conversion of paraffinic hydrocarbon is typically greater than about 50 mole percent, preferably, greater than about 60 mole percent, and more preferably, greater than about 70 mole percent.

Likewise, the selectivity to products will vary depending upon the specific feed composition, catalyst composition, reactor, and process conditions employed. For the purposes of this invention, "selectivity" is defined as the percentage of carbon atoms in the converted paraffin feed which react to form a specific product. For example, the olefin selectivity is calculated as follows:

$$\frac{\text{Moles of olefin formed} \times \text{Number of carbon atoms in olefin} \times 100}{\text{Moles of paraffin converted} \times \text{Number of carbon atoms in paraffin}}$$

Generally, the olefin selectivity increases with increasing temperature up to a maximum value and declines as the temperature continues to rise. Usually, the olefin selectivity does not change substantially over a wide range of high space velocities employed. In the process of this invention, the olefin selectivity is typically greater than about 50 carbon atom percent, preferably, greater than about 60 carbon atom percent, more preferably, greater than about 70 carbon atom percent, and even more preferably, greater than about 80 carbon atom percent. Other products formed in smaller quantities include methane, carbon monoxide, carbon dioxide, propane, butenes, butadiene, propadiene, aceylene, methylacetylene, and $C_{6+}$ hydrocarbons. Acetylene can be hydrogenated to ethylene downstream to increase the overall selectivity to olefin. At least part of the carbon monoxide, carbon dioxide, and methane formed may be recycled to the reactor.

Water is also formed in the process of this invention from the reaction of hydrogen or hydrocarbon. The presence of hydrogen in the feed minimizes the formation of carbon oxides by reacting with the oxygen to produce water and energy. Accordingly, it is advantageous to recycle the hydrogen in the product stream, obtained from the dehydrogenation of the paraffin, back to the reactor. Optimally, the hydrogen needed to meet the demands of the process essentially equals the hydrogen formed during conversion of the paraffin to olefin. Under these balanced conditions, the hydrogen forms a closed loop wherein there is essentially no demand for additional hydrogen to be added to the feed. Such conditions are more easily met when the feed is preheated and a higher hydrocarbon to oxygen molar ratio is employed.

The invention will be further clarified by a consideration of the following examples, which are intended to be purely illustrative of the use of the invention. Other embodiments of the invention will be apparent to those skilled in the art from a consideration of this specification or practice of the invention as disclosed herein. Unless otherwise noted, all percentages are given on a mole percent basis. Selectivities are given on a carbon atom percent basis.

EXAMPLE 1

(E-1)—Oxidation of Ethane to Ethylene—
Hydrogen and Pt/Sn Catalyst

A catalyst comprising platinum and tin supported on an alumina monolith was prepared by the following method. Platinum and tin were codeposited on a foam monolith (92 weight percent alpha alumina, 8 weight percent silica; 1.8 cm diameter×1 cm thick, 45 ppi (18 ppcm)) by impregnation with an aqueous solution of platinum and tin in a Pt:Sn atomic ratio of 1:5. The impregnation solution was prepared from a stock aqueous solution of hexachloroplatinic acid (0.193 M $H_2PtCl_6$) and a stock aqueous solution of stannous chloride (0.372 M $SnCl_2$) acidified with 5 weight percent hydrochloric acid. Sufficient impregnation solution was used to obtain a platinum loading of 1.3 weight percent. The impregnated monolith was dried in ambient air and then reduced under flowing hydrogen (5 volume percent in nitrogen) at a flow rate of 1 cubic foot per hour (cfh) (473 cm$^3$/min) using the following temperature profile: 1 h from ambient to 125° C., then 1 h from 125° C. to 300° C.; 1 h from 300° C. to 450° C., held for 30 min at 450° C. and then cooled to room temperature.

The catalyst was sandwiched between two inert alpha alumina monoliths which acted as radiation shields. The monoliths were sealed in a quartz tube using FiberFrax™ brand alumina-silica cloth (FiberFrax is a trademark of and available from Unifrax Corporation), and the reactor was insulated by wrapping the quartz tube with high temperature insulation. A feed comprising ethane (2.6 standard liters per minute (slpm)), oxygen (1.3 slpm), hydrogen (2.6 slpm) and nitrogen (1.147 slpm) was fed to the reactor. Total flow was 7.647 slpm (GHSV 180,305 h$^{-1}$) at 15 volume percent dilution with nitrogen. The ethane to oxygen molar ratio was 2:1; the hydrogen to oxygen molar ratio was 2:1.

The catalyst was operated autothermally and the heat generated by the reaction was sufficient to sustain the process. However, heat was needed initially to ignite the process. The procedure for light-off involved establishing the flows of nitrogen, ethane, and hydrogen, then adding the oxygen flow; and then heating the feed to 200° C. until ignition. This procedure ensured a fuel-rich feed for safety considerations. The light-off conditions were 7 slpm total gas flow, 2.24 slpm of ethane, 2.24 slpm of hydrogen, 1.12 slpm of oxygen, 1.40 slpm of nitrogen, 20 percent dilution with nitrogen, an ethane to oxygen molar ratio of 2:1, a hydrogen to oxygen molar ratio of 2:1, and a pressure of 1.34 atm abs (136 kPa abs). After light-off, the external heat source was removed, and the gas flow rates and pressure were adjusted to the desired conditions, as shown in Table 1. Pressure was maintained at 1.34 atm abs (136 kPa abs). Shutdown of the reactor was accomplished by turning off oxygen prior to alkane and hydrogen.

The product gases were analyzed on a Carle gas chromatograph designed for refinery gas analyses of components up to $C_6$ hydrocarbons. For quantitative determination of concentrations, standards were used for all species except water, which was obtained from an oxygen atom balance. Nitrogen was used as an internal GC calibration standard. Results are set forth in Table 1.

TABLE 1

Oxidation of Ethane to Ethylene with Pt Catalysts
Examples vs Comparative Experiments[a,b]

| | | % Carbon Atom Selectivities | | | | |
|---|---|---|---|---|---|---|
| Ex. # Catalyst | % $C_2H_6$ Conv. | $C_2H_4$ | CO | $CO_2$ | $CH_4$ | C3+ |
| CE-1a Pt - No $H_2$ | 62.3 | 61.1 | 22.60 | 7.75 | 4.05 | 4.50 |
| CE-1b Pt—$H_2$ | 62.2 | 71.1 | 16.92 | 1.40 | 6.10 | 4.48 |
| CE-1c Pt—Sn No $H_2$ | 65.9 | 67.6 | 17.65 | 6.40 | 3.80 | 4.55 |
| E-1 Pt—Sn $H_2$ | 69.6 | 81.1 | 7.29 | 0.34 | 6.28 | 4.99 |
| CE-2 Pt—Sb No $H_2$ | 68.0 | 68.3 | 17.70 | 6.40 | 3.95 | 3.65 |
| E-2 Pt—Sb $H_2$ | 69.5 | 81.5 | 7.56 | 0.27 | 6.32 | 4.35 |
| CE-3 Pt—Sn—Sb No $H_2$ | 66.5 | 68.0 | 17.03 | 6.57 | 3.87 | 4.53 |
| E-3 Pt—Sn—Sb $H_2$ | 68.5 | 80.6 | 8.27 | 0.46 | 6.10 | 4.57 |

[a]Feed with hydrogen: ethane (2.6 slpm), oxygen (1.3 slpm), hydrogen (2.6 slpm) and nitrogen (1.147 slpm); total flow 7.647 slpm (GHSV = 180,305 h$^{-1}$); 15% $N_2$ dilution; molar ratios: $C_2H_6/O_2$ = 2:1; $H_2/O_2$ = 2:1; autothermal conditions; pressure = 1.34 atm abs (136 kPa abs); no preheat.
[b]Feed without hydrogen: ethane (2.6 slpm); oxygen (1.3 slpm); nitrogen (2.1 slpm); total flow: 6.0 slpm (GHSV = 141,471 h$^{-1}$); 35% $N_2$ dilution; molar ratio $C_2H_6/O_2$ = 2:1; autothermal conditions; pressure = 1.34 atm abs (136 kPa abs); no preheat.

It was seen that a catalyst comprising platinum and tin supported on a ceramic monolith was active in the partial oxidation of ethane in the presence of hydrogen to produce ethylene. The catalyst achieved an ethane conversion of 69.6 percent and an ethylene selectivity of 81.1 percent. The ethane conversion and ethylene selectivity achieved were comparable to those" obtained from commercial thermal cracking furnaces. Very low amounts of carbon monoxide (7.29 percent) and carbon dioxide (0.34 percent) were found, as well as comparable amounts of methane and C3+ products. Carbon monoxide, carbon dioxide, and methane, at least in part, can be recycled to the reactor along with the hydrogen produced in the process.

Comparative Experiment 1
(CE-1a) and (CE-1b)

The oxidation of ethane was conducted under autothermal process conditions with a catalyst consisting of platinum supported on a ceramic monolith support. The catalyst was prepared as in E-1, with the exception that no tin was added to the catalyst. The process was conducted first in the absence of hydrogen (CE-1a) as noted hereinafter, and then, in the presence of hydrogen (CE-1b) in a manner similar to E-1. For the part of the experiment without hydrogen, the flow rates of the reactant feed were adjusted as follows: ethane (2.6 slpm); oxygen (1.3 slpm); nitrogen (2.1 slpm). Total flow was 6 slpm (GHSV=141,471 $h^{-1}$) at 35 volume percent nitrogen dilution. Molar ratio of ethane to oxygen was 2:1. This flow adjustment ensured that identical absolute amounts of ethane and oxygen were used with and without hydrogen. The level of nitrogen dilution was adjusted to ensure equivalent ethane conversions with and without hydrogen. Processes were conducted autothermally in the manner described in E-1 with the results shown in Table 1 (CE-1a and CE-1b).

It was seen that a catalyst consisting of pure platinum on an alumina monolith achieved an ethylene selectivity of 61.1 percent in the absence of hydrogen (CE-1a) and 71.1 percent in the presence of hydrogen (CE-1b) at similar ethane conversions. Thus, the addition of hydrogen improved ethylene selectivity. More significantly, when CE-1a and CE-1b were compared with E-1, it was found that the combined use of hydrogen in the feed and tin in the catalyst resulted in the highest ethane conversion and ethylene selectivity at significantly lower selectivities to carbon oxides.

(CE-1c) The oxidation of ethane was conducted as in E-1 with the exception that no hydrogen was used in the process, and the feed flow rates were adjusted as described in CE-1a. The catalyst used was identical to the catalyst of E-1. Results are shown in Table 1 (CE-1c). When the process of E-1, using a catalyst containing platinum and tin, was repeated in the absence of hydrogen, an ethylene selectivity of 67.6 percent was achieved at an ethane conversion of 65.9 percent. When E-1 was compared with CE-1c, it was seen that the combined use of hydrogen in the feed and tin in the catalyst gave the highest ethane conversion, the highest ethylene selectivity, and the lowest selectivities to carbon oxides.

EXAMPLE 2

(E-2)—Oxidation of Ethane to Ethylene—
Hydrogen and Pt/Sb Catalyst

A catalyst comprising platinum and antimony supported on an alumina monolith was prepared in a manner similar to that described in Example 1. The monolith of Example 1 was impregnated with an aqueous solution of platinum and antimony in a Pt:Sb atomic ratio of 1:5. The impregnation solution was prepared from a stock aqueous solution of hexachloroplatinic acid (0.193 M $H_2PtCl_6$) and a stock aqueous solution of antimony triacetate (0.182 M $Sb(OAc)_3$) containing hydrochloric acid sufficient to dissolve the antimony salt. Sufficient impregnation solution was used to obtain a platinum loading of 1.3 weight percent. The impregnated monolith was dried in ambient air, then reduced under flowing hydrogen in the manner described in E-1 hereinabove.

The catalyst was tested in the oxidation of ethane to ethylene in the presence of hydrogen and under autothermal process conditions as described in E-1 with the results shown in Table 1 hereinabove. It was seen that under autothermal process conditions a catalyst comprising platinum and antimony supported on a ceramic monolith achieved an ethane conversion of 69.5 percent and an ethylene selectivity of 81.5 percent. Selectivities to carbon monoxide and carbon dioxide were low. The results are comparable to those achieved in commercial thermal cracking furnaces.

Comparative Experiment 2 (CE-2)

The catalyst of E-2 comprising platinum and antimony supported on an alumina monolith was tested in the oxidation of ethane as described in E-2, with the exception that no hydrogen was used in the feedstream. Process conditions were as described in CE-1a. Results are set forth in Table 1 (CE-2).

When E-2 was compared with CE-2 or any of CE-1a and CE-1b, it was seen that the combined use of antimony in the catalyst and hydrogen in the feedstream as shown in E-2 gave the highest ethane conversion and ethylene selectivity and the lowest levels of carbon oxides.

EXAMPLE 3

(E-3)—Oxidation of Ethane to Ethylene—
Hydrogen and Pt/Sn/Sb Catalyst

A catalyst comprising platinum, tin, and antimony supported on an alumina monolith was prepared in a manner similar to that described in Examples 1 and 2. The metals were codeposited by impregnation of the support with an aqueous solution of Pt, Sn, and Sb salts in a Pt:Sn:Sb atomic ratio of 1:5:0.26. The impregnation solution was prepared from a stock aqueous solution of platinum hexachloroplatinic acid (0.193 M), a stock aqueous solution of stannous chloride (0.372 M) containing hydrochloric acid (5 weight percent), and a stock aqueous solution of antimony triacetate (0.182 M) containing hydrochloric acid (50 weight percent). Sufficient impregnation solution was used to obtain a platinum loading of 1.3 weight percent. The impregnated monolith was dried in ambient air and reduced under hydrogen as described in E-1 hereinabove.

The catalyst was tested in the oxidation of ethane to ethylene in the presence of hydrogen and under autothermal process conditions as described in E-1 with the results shown in Table 1 hereinabove. It was seen that a catalyst comprising platinum, tin, and antimony supported on a ceramic monolith achieved an ethane conversion of 68.5 percent and an ethylene selectivity of 80.6 percent. Carbon monoxide and carbon dioxide were produced only at low levels. The results are comparable to those achieved in commercial thermal cracking furnaces.

Comparative Experiment 3 (CE-3)

The catalyst of E-3 comprising platinum, tin, and antimony on an alumina monolith was evaluated in the oxidation of ethane as described in E-3, with the exception that no hydrogen was used in the feedstream. Process conditions were as described in CE-1a. Results are set forth in Table 1 (CE-3). When E-3 was compared with CE-3 and any of CE-1a and CE-1b, it was seen that the combined use of antimony and tin in the catalyst and hydrogen in the feedstream as shown in E-3 gave the highest conversion of ethane, the highest selectivity to ethylene, and the lowest levels of carbon oxides.

EXAMPLE 4

(E-4)—Oxidation of Ethane to Ethylene—Pt/Cu/ Fiber Monolith Catalyst

An aqueous impregnation solution was prepared containing platinum and copper in a Pt:Cu atomic ratio of 1:5. The impregnation solution was prepared from stock solutions of chloroplatinic acid (0.193 M $H_2PtCl_6$) and cupric chloride (1.49 M $CuCl_2$). A ceramic fiber mat (Nextel™ 440 brand fiber mat, 2 cm square×1 cm thick, weighing 0.25 g) was precalcined in air at 900° C., cooled, and then impregnated with the impregnation solution to saturation. Sufficient solution was used to obtain a calculated platinum loading of 16 weight percent in the finished mat. The impregnated fiber mat was dried in ambient air, then reduced in flowing hydrogen, as described in E-1.

The catalyst was sandwiched between two inert foam monoliths (1.8 cm dia by 1 cm thick, 18 ppcm alumina or mullite), wrapped in FiberFrax™ brand alumina-silica cloth, and packed into a quartz tube reactor (Inner Diameter (I.D.) 1.9 cm). The feed to the reactor was preheated with a heating tape wrapped around the quartz tube upstream of the catalyst. The catalyst zone was not heated, but was insulated with high temperature insulation material to minimize heat losses. Ethane, hydrogen, and nitrogen were preheated to 200° C. and fed to the reactor. Oxygen was then introduced to the reactor which resulted in catalyst ignition. Upon ignition the temperature rose within a few seconds to 1000° C., and the reactor operated autothermally. Process conditions and results are shown in Table 2.

TABLE 2

Ethane Oxidation to Ethylene Over Catalyst of Pt/Cu on Fiber Monolith

| E-4 | Run 1[a] | Run 2[a] |
|---|---|---|
| Total Feed Flow, slpm | 6.75 | 8.0 |
| GHSV, h$^{-1}$ | 318,471 | 377,448 |
| $N_2$ Dilution | 12% | 30% |
| Molar Ratio $C_2H_6/O_2$ | 2.2 | 2.0 |
| Molar Ratio $H_2/O_2$ | 2.2 | 2.0 |
| % $C_2H_6$ Conv | 70.0 | 71.2 |
| % CO Sel | 7.5 | 7.8 |
| % $CO_2$ Sel | 0.6 | 0.7 |
| % $C_2H_4$ Sel | 80.0 | 80.4 |
| % $C_2H_2$ Sel | 1.0 | 1.2 |
| % Total $C_2H_4$ Sel | 81.0 | 81.6 |

[a]Feed preheated at 200° C.; pressure = 1.35 atm abs (137 kPa).

It was found that a catalyst comprising platinum and copper supported on a ceramic fiber monolith achieved an ethane conversion of about 70 percent and an ethylene selectivity of 80 percent. Carbon monoxide and carbon dioxide were produced only at low levels. The results are comparable to those achieved in commercial thermal cracking furnaces.

EXAMPLE 5

(E-5)—Oxidation of Ethane to Ethylene—Catalyst Stability

Five catalysts were prepared as follows:

Catalyst A comprised platinum and copper in a Pt:Cu atomic ratio of 1:1 supported on an alumina foam monolith. The monolith of E-1 was impregnated with an aqueous impregnation solution (1 ml) prepared from stock solutions of hexachloroplatinic acid (0.193 M) and cupric chloride (1.49 M). Sufficient stock solutions were used to achieve a Pt:Cu atomic ratio of 1:1. Calculated platinum loading was 1.2 weight percent. The impregnated monolith was dried and reduced under hydrogen in the manner described in E-1.

Catalyst B comprised platinum and copper in a Pt:Cu atomic ratio 1:1 supported on a Nextel™ 440 ceramic fiber mat. The catalyst was prepared in the manner described in E-4 hereinabove, with the exception that the amounts of stock solutions used were adjusted to provide the Pt:Cu atomic ratio of 1:1. Calculated platinum loading was 20 weight percent.

Catalyst C comprised platinum and copper in an atomic ratio of 1:2 supported on a Nextel™ 440 ceramic fiber mat. The catalyst was prepared in the manner described in E-4 hereinabove, with the exception that the amounts of stock solutions used were adjusted to give the Pt:Cu atomic ratio of 1:2. Calculated platinum loading was 24 weight percent.

Catalyst D comprised platinum, tin, and copper in an atomic ratio 1:1:1 supported on a Nextel™ 440 ceramic fiber mat. The catalyst was prepared by calcining the fiber mat at 900° C., cooling, then impregnating the calcined mat to wetness with an impregnation solution prepared from stock solutions of hexachloroplatinic acid (0.193 M), cupric chloride (1.49 M), and stannous chloride (0.372 M) acidified with 5 weight percent hydrochloric acid. Calculated platinum loading was 18 weight percent. The impregnated fiber mat was dried in ambient air and reduced under hydrogen, as described in E-1 hereinbefore.

Catalyst E comprised platinum and tin in an atomic ratio of 1:5 supported on a Nextel™ 440 brand ceramic fiber mat. The catalyst was prepared by calcining the fiber mat at 900° C., cooling, and impregnating the fiber mat to saturation with an aqueous impregnation solution prepared from stock solutions of hexachloroplatinic acid (0.193 M) and stannous chloride (0.372 M) acidified with hydrochloric acid (5 weight percent). Calculated platinum loading was 8.5 weight percent. The impregnated fiber mat was dried and reduced as described in E-1 hereinbefore.

The catalysts were tested in the oxidation of ethane to ethylene in the presence of hydrogen and under autothermal reaction conditions. Process conditions and results are set forth in Table 3.

TABLE 3

Oxidation of Ethane to Ethylene - Stability of Catalysts[a]

| Catalyst | Flow slpm | GHSV h$^{-1}$ | % $N_2$ | % $C_2H_4$ Sel | % $C_2H_6$ Conv | TOS[b] h |
|---|---|---|---|---|---|---|
| A: Pt—Cu (1:1) on $Al_2O_3$ foam | 7.33 | 172,830 | 20.5 | 79.1 | 63.1 | 2.0 |
| | | | | 78.9 | 63.0 | 13.7 |
| B: Pt—Cu (1:1) | 8.33 | 392,959 | 30 | 82.2 | 58.5 | 1 |

TABLE 3-continued

Oxidation of Ethane to Ethylene - Stability of Catalysts[a]

| Catalyst | Flow slpm | GHSV h$^{-1}$ | % N$_2$ | % C$_2$H$_4$ Sel | % C$_2$H$_6$ Conv | TOS[b] h |
|---|---|---|---|---|---|---|
| on fiber mat | | | | 81.1 | 56.5 | 8 |
| C: Pt—Cu (1:2) | 8.33 | 392,959 | 30 | 82.5 | 60.9 | 0.5 |
| on fiber mat | | | | 81.6 | 59.3 | 17.3 |
| D: Pt—Sn—Cu (1:1:1) | 8.33 | 392,959 | 30 | 83.7 | 61.2 | 0.3 |
| on fiber mat | | | | 81.6 | 59.3 | 18 |
| E: Pt—Sn (1:5) | 8.33 | 392,959 | 30 | 83.2 | 59.4 | 2 |
| on fiber mat | | | | 82.0 | 55.1 | 18 |

[a]Feed: ethane, oxygen, hydrogen, nitrogen. Total flow as shown; % N$_2$ = mole percentage of feedstream which is nitrogen; molar ratios: C$_2$H$_6$/O$_2$ = 2:1, H$_2$/O$_2$ = 2:1; no preheat; autothermal process conditions; pressure = 1.34 atm abs (136 kPa).
[b]TOS = time on stream.

It was found that catalysts comprising platinum and tin, copper, or a mixture thereof, supported on a ceramic foam or fiber mat achieved a high ethane conversion, a high ethylene selectivity, and good catalyst stability in a process of oxidizing ethane to ethylene in the presence of hydrogen.

EXAMPLE 6

(E-6)—Oxidation of Ethane to Ethylene—Variation in Pt/Cu Ratio

Catalysts comprising platinum and copper supported on Nextel™ 440 brand ceramic fiber mats were prepared in the manner described in E-4 hereinabove. The atomic ratio of platinum to copper was varied from 1:0.1 to 1:5. The catalysts were tested in the oxidation of ethane to ethylene in the presence of hydrogen and under autothermal process conditions, with the results shown in Table 4.

TABLE 4

Oxidation of Ethane to Ethylene Variation in Pt/Cu Ratio[a]

| Pt:Cu ratio | Pt loading (wt %) | TOS[b] h | % C$_2$H$_4$ Sel. | % C$_2$H$_6$ Conv. |
|---|---|---|---|---|
| 1:0.1 | 21 | 2.1 | 79.3 | 55.1 |
| 1:0.5 | 21 | 8.5 | 80.3 | 56.2 |
| 1:1 | 20 | 8.0 | 81.1 | 56.5 |
| 1:2 | 24 | 16.3 | 81.6 | 59.3 |
| 1:3 | 21 | 16.5 | 81.7 | 59.4 |
| 1:5 | 18 | 15.5 | 82.1 | 59.3 |

[a]Feed: ethane, oxygen, hydrogen, nitrogen. Total Flow = 8.33 slpm (GHSV = 392,959 h$^{-1}$), 30%-nitrogen dilution; molar ratios: C$_2$H$_6$/O$_2$ = 2:1, H$_2$/O$_2$ = 2:1; no preheat; autothermal conditions; pressure = 1.32 atm abs (134 kPa).
[b]TOS = time on stream (h).

Samples run out to 8 or less hours would have given slightly lower conversion and selectivity if run out to 16 hours. Thus, it was found that as the atomic ratio of platinum to copper decreased from 1:0.1 to 1:5, the ethane conversion and ethylene selectivity increased. It was also found that at the higher concentrations of copper, the catalyst did not remain lit in the absence of hydrogen.

EXAMPLE 7

(E-7)—Oxidation of Ethane to Ethylene—Variation in Space Velocity

A catalyst comprising platinum and copper in an atomic ratio of 1:1 supported on a Nextel™ 440 brand ceramic fiber mat was prepared in a manner similar to that described in E-4 hereinabove. The catalyst was evaluated in the oxidation of ethane to ethylene in the presence of hydrogen under autothermal process conditions. The gas hourly space velocity of the total feed was progressively increased at constant pressure with the results shown in Table 5.

TABLE 5

Oxidation of Ethane to Ethylene Variation in Space Velocity[a]

| Flow rate slpm | GHSV h$^{-1}$ | % C$_2$H$_4$ Sel. | % C$_2$H$_6$ Conv. |
|---|---|---|---|
| 7 | 330,100 | 80.6 | 54.3 |
| 14 | 660,200 | 81.0 | 55.7 |
| 21 | 990,300 | 81.7 | 55.5 |
| 28 | 1,320,400 | 81.6 | 55.7 |
| 35 | 1,650,500 | 82.4 | 53.0 |
| 42 | 1,980,600 | 81.9 | 52.4 |

[a]Feed: ethane, oxygen, hydrogen, nitrogen; 25% nitrogen dilution; molar ratios: C$_2$H$_6$/O$_2$ = 2:1, H$_2$/O$_2$ = 2:1; no preheat, autothermal conditions; pressure = 1.68 atm abs (170 kPa).

Over a wide range of space velocities tested, it was found that the ethane conversion and ethylene selectivity did not change significantly.

EXAMPLE 8

(E-8)—Oxidation of Ethane to Ethylene—Modified Support

Four catalysts were prepared comprising platinum supported on a modified ceramic foam monolith (92 weight percent alpha alumina, 8 weight percent silica; 45 ppi (18 ppcm); 1.8 cm dia by 1 cm thick; average weight 2.8 g). The preparation was characterized by first modifying the support with a support modifier, specifically tin or antimony, and then depositing platinum and optionally copper on the modified support. In this example, the same element (Sn) that modifies the support also functions as a promoter. Details of the preparation were as follows:

Catalyst A comprised platinum on a tin-modified alumina monolith. The monolith of E-1 was impregnated to wetness with an aqueous solution of stannous chloride (0.372 M) containing 5 weight percent hydrochloric acid. The impregnated support was air dried and then reduced at 700° C. under flowing hydrogen at a flow rate of 1 cfh (473 cm$^3$/min). The modified support was impregnated with an aqueous solution (1 ml) of hexachloroplatinic acid (0.193 M), then dried in ambient air and reduced under hydrogen as described in E-1.

Catalyst B comprised platinum and copper (1:1) on a tin-modified alumina monolith. The monolith was impregnated to wetness with an aqueous solution of stannous chloride (0.372 M) containing hydrochloric acid (5 weight percent). The tin-impregnated monolith was air dried and reduced at 700° C. for 2 h in flowing hydrogen (5 volume percent in nitrogen) at a flow rate of 1 cfh (473 cm$^3$/min). The modified monolith was impregnated with an aqueous solution (1 ml) prepared from stock solutions of hexachloroplatinic acid (0.193 M) and cupric chloride (1.49 M). The impregnated monolith was air dried and reduced under flowing hydrogen as described in E-1.

Catalyst C comprised platinum and copper (1:5) on a tin-modified alumina monolith. The catalyst was prepared as in "B" hereinabove with the exception that sufficient stock solutions were used to give a Pt:Cu atomic ratio of 1:5.

Catalyst D comprised platinum and copper (1:5) on an antimony-modified alumina monolith. In this example, the monolith comprised alpha alumina (99.5 weight percent). The monolith was impregnated to wetness with a solution of antimony triacetate (0.182 M) dissolved in hydrochloric acid. The monolith was air dried and reduced for 2 h at 700° C. under flowing hydrogen (5 volume percent in nitrogen) at a flow rate of 1 cfh (473 cm³/min). The reduced monolith was impregnated with an aqueous impregnation solution (1 ml) prepared from a stock solution of hexachloroplatinic acid (0.193 M, 1 ml) and a stock solution of cupric chloride (1.49 M, 0.65 ml). The monolith was dried in air and reduced as in E-1.

The catalysts were evaluated in the oxidation of ethane in the presence of hydrogen and under autothermal reaction conditions with the results shown in Table 6.

TABLE 6

Oxidation of Ethane to Ethylene - Modified Support[a]

| Catalyst | Flow slpm | GHSV h$^{-1}$ | % N$_2$ | C$_2$H$_6$ O$_2$ | H$_2$ O$_2$ | Pre-heat °C. | % C$_2$H$_4$ Sel. | % C$_2$H$_6$ Conv | TOS[b] h |
|---|---|---|---|---|---|---|---|---|---|
| A: Pt Sn—Al$_2$O$_3$ foam | 11 | 259,364 | 5 | 2.1 | 2.1 | 150 | 78.3 | 68.1 | 0.5 |
|  |  |  |  |  |  | 150 | 76.6 | 67.5 | 7.5 |
| B: Pt—Cu (1:1) Sn—Al$_2$O$_3$ foam | 11 | 259,364 | 5 | 2.1 | 2.1 | 150 | 79.8 | 71.1 | 0.5 |
|  |  |  |  |  |  | 150 | 78.8 | 69.7 | 15 |
| C: Pt—Cu (1:5) Sn—Al$_2$O$_3$ foam | 7 | 159,155 | 12 | 2.2 | 2.2 | 200 | 81.4 | 69.8 | 5 |
|  |  |  |  |  |  | 200 | 81.0 | 69.1 | 21 |
| D: Pt—Cu (1:5) Sb—Al$_2$O$_3$ foam | 7 | 165,050 | 10 | 2.3 | 2.3 | 250 | 82.0 | 67.8 | 2.5 |
|  |  |  |  |  |  | 250 | 81.8 | 67.4 | 15 |

[a]Feed: ethane, oxygen, hydrogen, nitrogen; total flow, nitrogen dilution, and molar ratios of C$_2$H$_6$/O$_2$ and H$_2$/O$_2$ as shown; preheat as shown; autothermal conditions; pressure = 1.34 atm abs (136 kPa).
[b]TOS = time on stream (h).

It was found that a catalyst comprising platinum and optionally copper supported on a ceramic foam monolith modified with tin or antimony achieved a high conversion of ethane, a high selectivity to ethylene, and good catalyst stability. Results are comparable to those obtained from a commercial cracking furnace.

EXAMPLE 9

(E-9)—Oxidation of a Natural Gas Liquid Feed

A catalyst comprising platinum and copper (1:2) on a tin-modified alumina monolith (92 weight percent alumina) was prepared in the manner described in Example 8B, with the exception that the atomic ratio of Pt:Cu was adjusted to 1:2. This catalyst was evaluated in the oxidation of a natural gas liquid (NGL) feed in the presence of hydrogen under autothermal process conditions. The liquid feed composition, an Algerian condensate, comprised on a weight percent basis a mixture of 42.1 percent paraffins, 34.4 percent isoparaffins, 7.3 percent aromatics, 12.3 percent naphthenes, 0.2 percent oxygenates, and the balance (about 3–4 percent) unidentified components. The alkanes comprised C$_{1-19}$ alkanes having a maximum molar concentration in the C$_{5-8}$ range. Feed was preheated at 200° C. Total gas flow was about 8 slpm (GHSV 200,000 h$^{-1}$). Process conditions and results are set forth in Table 7.

TABLE 7

Oxidation of Natural Gas Liquid Feed (NGL)[a,b]

| Liq. feed gm/min | O$_2$ slpm | H$_2$ slpm | N$_2$ slpm | CH$_4$ NGL | C$_2$H$_4$ NGL | C$_2$H$_6$ NGL | C$_3$H$_8$ NGL | C$_4$H$_6$ NGL | C$_{6+}$ NGL |
|---|---|---|---|---|---|---|---|---|---|
| 3.2 | 1.2 | 3.2 | 2.0 | 0.17 | 0.38 | 0.10 | 0.026 | 0.033 | 0.09 |
| 3.2 | 1.1 | 3.2 | 2.0 | 0.135 | 0.33 | 0.14 | 0.050 | 0.039 | 0.11 |
| 3.15 | 1.3 | 3.2 | 2.6 | 0.176 | 0.39 | 0.08 | 0.021 | 0.031 | 0.092 |
| 3.15 | 1.2 | 3.2 | 2.6 | 0.149 | 0.36 | 0.13 | 0.043 | 0.039 | 0.099 |

[a]Feed composition: C$_{1-9}$ alkanes (76.5 wt %), maximum molar range C$_{5-8}$; autothermal conditions; 200° C. preheat; pressure = 1.34 atm abs (136 kPa); GHSV = 200,000 h$^{-1}$.
[b]Selectivities given in g product per g NGL in the feed.

It was seen that a catalyst comprising platinum and copper on a ceramic monolith support was capable of oxidizing a natural gas liquid feed in the presence of hydrogen under autothermal conditions to a mixture of low molecular weight olefins, specifically, ethylene, propylene, butylene, and butadiene.

EXAMPLE 10

(E-10)—Oxidation of Ethane to Ethylene—Pt—Cu Catalyst on Modified Support

Catalysts were prepared comprising platinum and copper supported on a modified ceramic foam monolith. The preparation was characterized by first modifying the support with tin and optionally a second modifier, and thereafter depositing platinum and copper on the modified support. The support comprised a foam monolith, either 92 or 99.5 weight percent alumina [1.8 cm dia×1 cm thick; 45 ppi (18 ppcm)]. Preparations were as follows:

Catalyst A comprising platinum and copper (1:2) on a tin-modified alumina (92 weight percent) was prepared in the manner described in Example 8B, with the exception that the atomic ratio of Pt:Cu was adjusted to 1:2. Catalyst B comprising platinum and copper (1:5) on a tin-modified alumina (92.0 weight percent) was prepared as in Example 8C. Catalyst C comprising platinum and copper (1:4) on a tin-modified alumina (99.5 weight percent) was prepared in the manner described in Example 8B, with the exception that the atomic ratio of Pt:Cu was adjusted to 1:4. Catalyst D comprising platinum and copper (1:5) on a tin-modified alumina (99.5 weight percent) was prepared as in Example 8C.

Catalyst E comprised platinum and copper (1:5) on a tin and calcium-modified alumina monolith (99.5 weight percent). The monolith was immersed in a saturated aqueous solution of calcium hydroxide for 24 h. Then, the monolith was rinsed several times with distilled water, air dried, and calcined at 900° C. for 1 h. The calcined monolith was immersed in an aqueous solution of stannous chloride (0.372 M) containing hydrochloric acid (5 weight percent) for several hours, after which the monolith was air dried and reduced under flowing hydrogen (1 cfh; 473 cm$^3$/min) at 700° C. for 2 h. An aqueous impregnation solution having a Pt:Cu atomic ratio of 1:5 was prepared from stock solutions comprising hexachloroplatinic acid (1 ml, 0.193 M) and cupric chloride (0.65 ml, 1.49 M). The monolith was impregnated with the impregnation solution (1 ml). The impregnated monolith was dried in ambient air and reduced as in E-1.

Catalyst F comprised platinum and copper (1:5) on a tin and zirconium-modified alumina monolith (99.5 weight percent). The monolith was immersed for 24 h in an aqueous solution of zirconium oxychloride (ZrOCl$_2$, 1M) containing 1 weight percent hydrochloric acid. The monolith was rinsed with distilled water, air dried, and calcined at 900° C. for 1 h. The calcined monolith was immersed for several hours in an aqueous solution of stannous chloride (0.372 M) containing hydrochloric acid (5 weight percent), after which the monolith was air dried and reduced under flowing hydrogen (1 cfh; 473 cm$^3$/min) at 700° C. for 2 h. An impregnation solution containing platinum and copper (1:5) was prepared from stock solutions of hexachloroplatinic acid (1 ml, 0.193 M) and cupric chloride (0.65 ml, 1.49 M). The monolith was impregnated with the impregnation solution (1 ml), dried in air, and reduced as in E-1.

Catalyst G comprised platinum and copper (1:5) on a tin and lanthanum-modified alumina foam monolith (99.5 weight percent). The monolith was immersed for 24 h in an aqueous solution of lanthanum chloride (1 M) containing 1 weight percent hydrochloric acid. The monolith was rinsed with distilled water several times, air dried, and then calcined at 900° C. for 1 h. The calcined monolith was cooled and then immersed in an aqueous solution of stannous chloride (0.372 M) containing hydrochloric acid (5 weight percent) for several hours, after which the monolith was air dried and reduced under flowing hydrogen (1 cfh; 473 cm$^3$/min) at 700° C. for 2 h. The modified monolith was impregnated with an impregnation solution (1 ml) containing platinum and copper (1:5) prepared from the stock solutions noted hereinbefore. The impregnated monolith was reduced under hydrogen as in E-1.

The catalysts were evaluated in the oxidation of ethane in the presence of hydrogen under autothermal reaction conditions with the results shown in Table 8.

TABLE 8

Oxidation of Ethane to Ethylene
Catalyst of Pt—Cu on Modified Support[a]

| Catalyst | Flow slpm | GHSV h$^{-1}$ | % N$_2$ | Preheat ° C. | % C$_2$H$_4$ Sel | % C$_2$H$_6$ Conv | TOS[b] h |
|---|---|---|---|---|---|---|---|
| A: Pt—Cu (1:2) Sn—Al$_2$O$_3$ (92%) | 7.0 | 165,050 | 10 | 300 | 79.9 | 71.3 | 7.2 |
| B: Pt—Cu (1:5) Sn—Al$_2$O$_3$ (92.0%) | 7.0 | 165,050 | 10 | 300 | 80.2 | 71.6 | 13 |
| C: Pt—Cu (1:4) Sn—Al$_2$O$_3$ (99.5%) | 8.3 | 196,409 | 5 | 300 | 81.0 | 71.9 | 4.5 |
| D: Pt—Cu (1:5) Sn—Al$_2$O$_3$ (99.5%) | 7.0 | 165,050 | 10 | 300 | 80.7 | 72.4 | 12 |
| E: Pt—Cu (1:5) Sn—Ca—Al$_2$O$_3$ (99.5%) | 8.3 | 196,409 | 5 | 250 | 81.5 | 71.4 | 0.3 |
| F: Pt—Cu (1:5) Sn—Zr—Al$_2$O$_3$ (99.5%) | 8.3 | 196,409 | 5 | 250 | 81.0 | 71.7 | 0.3 |
| G: Pt—Cu (1:5) Sn—La—Al$_2$O$_3$ (99.5%) | 8.3 | 196,409 | 5 | 250 | 81.7 | 71.2 | 0.5 |

[a]Feed: ethane, oxygen, hydrogen, and nitrogen. Total flow and nitrogen dilution as shown; molar ratios: C$_2$H$_6$/O$_2$ = 2.3:1, H$_2$/O$_2$ = 2.3:1; preheat as shown; autothermal conditions; pressure = 1.34 atm abs (136 kPa).
[b]TOS = time on stream (h).

It was seen that a catalyst comprising platinum and copper supported on an alumina monolith which had been pretreated with at least one of tin, calcium, zirconium, and lanthanum achieved a high ethane conversion, a high ethylene selectivity, and good stability in the oxidation of ethane to ethylene in the presence of hydrogen. Results of this invention are comparable to those obtained from commercial thermal cracking furnaces.

EXAMPLE 11

(E-11)—Oxidation of Ethylene—Variation with Pressure

The catalyst of E-7 was evaluated in the partial oxidation of ethane to ethylene in the presence of hydrogen in the manner described in E-7, with the exception that the pressure in the reactor was varied from about 2 atm abs (200 kPa abs) to about 4 atm abs (400 kPa abs). As in E-7, the catalyst comprised platinum and copper in an atomic ratio 1:1 supported on a Nextel™ 440 brand fiber mat. Process conditions and results are set forth in Table 9.

TABLE 9

Oxidation of Ethane-Variation in Pressure[a,b]

| Flow rate slpm | GHSV h$^{-1}$ | % N$_2$ dilution | Pressure kPa | % C$_2$H$_4$ Sel. | % C$_2$H$_6$ Conv. |
|---|---|---|---|---|---|
| 49 | 2,310,770 | 25 | 214 | 80.8 | 55.6 |
| 56 | 2,640,800 | 25 | 249 | 79.6 | 57.6 |
| 61 | 2,886,017 | 23 | 406 | 76.4 | 60.2 |
| 45 | 2,122,071 | 20 | 406 | 76.1 | 62.4 |
| 40 | 1,886,286 | 10 | 406 | 72.9 | 67.3 |

[a]Feed: ethane, oxygen, hydrogen, nitrogen; 25% nitrogen dilution; molar ratios: C$_2$H$_6$/O$_2$ = 2:1, H$_2$/O$_2$ = 2:1; no preheat, autothermal conditions.
[b]Catalyst: Pt/Cu (1:1) supported on Nextel ™ 440 fiber mat.

It was seen that as the pressure of the process increased, the ethane conversion increased and the ethylene selectivity decreased.

EXAMPLE 12

(E-12)—Partial Oxidation of Propane to Ethylene and Propylene

Two catalysts were evaluated in the partial oxidation of propane to ethylene and propylene in the presence of hydrogen. Catalyst A, identical to Catalyst E-1 hereinabove, comprised platinum and tin in an atomic ratio 1:5 supported on an alumina foam monolith (92 weight percent). Feed comprised a mixture of ethane (70 volume percent) and propane (30 volume percent) at a nitrogen dilution of 21 percent. Other process conditions and results are shown in Table 10.

Catalyst B, identical to Catalyst E-3 hereinabove, comprised platinum, tin, and antimony in an atomic ratio of 1:5:0.26 supported on an alumina foam monolith (92 weight percent). Feed comprised propane at a nitrogen dilution of 30 percent. Process conditions and results are shown in Table 10.

TABLE 10

Partial Oxidation of Propane to Propylene and Ethylene With Hydrogen and Multi-Metallic Catalyst

| Feed Conditions[a,b] | Mol % Conversion %  $C_2H_6$ Conv | Mol % Conversion %  $C_3H_8$ Conv | % Carbon Atom Selectivities $C_2H_4$ | $C_3H_6$ | CO | $CO_2$ | $CH_4$ | C4+ |
|---|---|---|---|---|---|---|---|---|
| A[a]. 70/30 $C_2H_6$/$C_3H_8$ | 71.8 | 94.6 | 65.2 | 3.5 | 12.6 | 0.6 | 14.2 | 3.0 |
| B[b]. 100% $C_3H_8$ | | | | | | | | |
| (1) Comparative[b] | — | 71.9 | 35.0 | 22.8 | 12.3 | 8.2 | 14.2 | 5.1 |
| (2)[b] | — | 77.5 | 41.5 | 20.7 | 10.1 | 1.0 | 18.0 | 5.5 |
| (3)[b] | — | 67.8 | 39.5 | 25.4 | 8.6 | 1.1 | 16.8 | 5.7 |

[a]Catalyst A: Pt/Sn (1:5) on alumina foam monolith; feed: ethane (70 vol %) and propane (30 vol %); 21% nitrogen dilution; total flow = 10 slpm; molar ratios: $C_2H_6/O_2$ = 1.05:1, $C_3H_8/O_2$ = 0.45:1, $H_2/O_2$ = 1.5:1.
[b]Catalyst B: Pt/Sn/Sb (1:5:0.26) on alumina foam monolith; (1) Propane feed; 30% nitrogen dilution; total flow = 7 slpm; molar ratio: $C_3H_8/O_2$ = 1.3:1; comparative. (2) Propane feed; 23% nitrogen dilution; total flow = 9 slpm; molar ratio: $C_3H_8/O_2$ = 1.3:1, $H_2/O_2$ =0 1.0:1. (3) Propane feed; 23% nitrogen dilution; total flow = 9 slpm; molar ratio: $C_3H_8/O_2$ = 1.4:1, $H_2/O_2$ = 1.0:1.

It was seen that propane is converted primarily to ethylene and propylene in the presence of hydrogen and a multi-metallic catalyst supported on an alumina monolith. When the Comparative Experiment 12-B1 is compared with Examples 12-B2 and 12-B3, it is seen that the total selectivity to ethylene and propylene is higher when hydrogen is co-fed.

EXAMPLE 13

(E-13)—Ethane to Ethylene with Preheat

A catalyst comprising platinum and copper on a tin and lanthanum-modified alumina monolith support was prepared as in Example E-10G. The catalyst was evaluated in the autothermal partial oxidation of ethane to ethylene under the conditions shown in Table 11. The feed comprising ethane, oxygen, hydrogen, and nitrogen was preheated to temperatures ranging from 281° C. to 589° C. At preheat tempera tures above 400° C., the molar ratio of ethane to oxygen was raised to 2.7:1 and higher. Results are set forth in Table 11.

TABLE 11

Autothermal Oxidation Of Ethane to Ethylene Using Preheat[a]

| $C_2H_6/O_2$ | $H_2/O_2$ | T (° C.) Preheat | % $C_2H_6$ Conv | % $C_2H_4$ Sel | % $CH_4$ Sel | % CO Sel | % $CO_2$ Sel | Net $H_2/C_2H_4$ |
|---|---|---|---|---|---|---|---|---|
| 2.3 | 2.3 | 281 | 70.4 | 80.00 | 6.67 | 8.20 | 0.55 | 0.004 |
| 2.7 | 2.7 | 488 | 67.7 | 81.80 | 6.30 | 6.90 | 0.53 | 0.12 |
| 2.7 | 2.7 | 538 | 70.1 | 81.22 | 6.66 | 7.33 | 0.53 | 0.18 |
| 2.8 | 2.8 | 589 | 69.7 | 81.46 | 6.65 | 7.23 | 0.53 | 0.21 |

[a]Feedstream: $C_2H_6$/O2 and $H_2/O_2$ molar ratios as shown; 10% nitrogen dilution; pressure = 1.35 bar abs (135 kPa); GHSV, in the range 180,000 to 200,000 h$^{-1}$; flow rate in the range 7.7 to 8.4 slpm; autothermal process conditions.

It was found that by preheating the feed to temperatures above 400° C., substantially the same ethane conversion and product selectivities were obtained at higher hydrocarbon to oxygen molar ratios, as were obtained at lower preheat and lower hydrocarbon to oxygen ratios. Compare, for example, the run at 281° C. preheat with the run at 538° C. preheat. The ethane conversion and ethylene selectivity were similar while oxygen usage dropped from 0.88 g O2 per g ethylene (ethane/oxygen molar ratio of 2.3:1) to 0.76 g O2 per g ethylene (ethane/oxygen molar ratio 2.7:1.) Likewise, the net hydrogen balance per mole ethylene improved from about zero (0.004) at 281° C. to 0.18 at 538° C.

EXAMPLE 14

(E-14)—Autothermal Oxidation of Ethane to Ethylene Using Pt/Cu on Magnesia Pellets A catalyst was prepared as in Example E-4 hereinabove, with the exception that magnesia pellets (Norton; 3 mm dia×5 mm length cylinders) were used in place of the alumina fiber mat support. The magnesia pellets were heated to 1200° C. for 16 h to reduce the surface area to less than 1 m$^2$/g. A solution containing platinum and copper in an atomic ratio of 1:5 was prepared using hexachloroplatinic acid and cupric chloride. The pellets were loaded with the solution, dried at 80° C. overnight, and reduced at 450° C. under hydrogen (5 volume percent) in nitrogen. Pt:Cu atomic ratio was 1:5.6. Pt loading, 0.57 weight percent; copper loading, 1.03 weight percent; balance magnesia.

The catalyst particles were sandwiched between two inert alumina monoliths in a quartz tube reactor. Catalyst bed dimensions were 17 mm (dia) by 15 mm (depth). The catalyst was evaluated in the autothermal oxidation of ethane to ethylene in the manner described hereinbefore. Process conditions and results are set forth in Table 12.

TABLE 12

Ethane Autothermal Oxidation to Ethylene with Pt/Cu/MgO Pelleted Catalyst[a]

| Time h | $C_2H_6/O_2$ | $H_2/O_2$ | % $C_2H_6$ Conv | % $C_2H_4$ Sel | % $CH_4$ Sel | % CO Sel | % $CO_2$ Sel |
|---|---|---|---|---|---|---|---|
| Preheat, 250° C.; 8 slpm[b] | | | | | | | |
| 0.9 | 2.3 | 2.3 | 73.6 | 79.6 | 7.5 | 5.4 | 2.2 |
| 4.5 | 2.3 | 2.3 | 73.5 | 80.0 | 7.0 | 5.4 | 2.0 |
| 6.2 | 2.3 | 2.3 | 73.7 | 79.4 | 6.9 | 5.5 | 2.0 |
| 7.2 | 2.3 | 2.3 | 73.7 | 79.5 | 7.0 | 5.6 | 2.0 |

TABLE 12-continued

Ethane Autothermal Oxidation to Ethylene
with Pt/Cu/MgO Pelleted Catalyst[a]

| Time h | $C_2H_6/O_2$ | $H_2/O_2$ | % $C_2H_6$ Conv | % $C_2H_4$ Sel | % $CH_4$ Sel | % CO Sel | % $CO_2$ Sel |
|---|---|---|---|---|---|---|---|
| Preheat, 275° C.; 6 slpm[b]; stable after 10 h | | | | | | | |
| 10.3 | 2.3 | 2.3 | 73.3 | 80.0 | 6.6 | 5.6 | 2.2 |
| Preheat, 250° C. at 2.5 h and 275° C. at 3.5 h; 8 slpm[b] | | | | | | | |
| 2.5 | 2.4 | 2.4 | 69.3 | 82.0 | 6.4 | 4.7 | 1.8 |
| 3.5 | 2.4 | 2.4 | 70.8 | 81.5 | 6.6 | 4.9 | 1.8 |

[a]Feedstream: $C_2H_6/O_2$ and $H_2/O_2$ as shown; 5% $N_2$ dilution; preheat as shown; pressure 1.35 bar abs (135 kPa); calculated adiabatic temperature = 950–1,050° C.; autothermal process conditions.
[b]6 slpm = GHSV 94,314 h$^{-1}$; 8 slpm = 125,752 h$^{-1}$.

It was found that magnesia pellets can be suitably employed as a catalyst support in the autothermal oxidation process of this invention.

EXAMPLE 15

(E-15), Oxidation of Ethane to Ethylene Using Catalyst of Pt—Cu on Magnesia Monolith Support A catalyst comprising platinum and copper on a ceramic monolith was prepared in the manner described in Example E-4, with the exception that a magnesia monolith (Hi-Tech Ceramics, 17 mm dia×10 mm width, 45 ppi) was used in place of the alumina fiber mat. Pt:Cu atomic ratio was 1:5, and the total metal loading was 5.67 weight percent. The catalyst was evaluated in the autothermal oxidation of ethane to ethylene as described hereinbefore, with the results shown in Table 13.

TABLE 13

Autothermal Oxidation of Ethane
to Ethylene Using Pt/Cu on MgO Monolith[a]

| Time (h) | % $C_2H_6$ Conv | % $C_2H_4$ Sel | % $CH_4$ Sel | % CO Sel | % $CO_2$ Sel |
|---|---|---|---|---|---|
| 0.5 | 75.1 | 80.0 | 6.7 | 6.0 | 1.8 |
| 1.5 | 75.1 | 80.7 | 6.5 | 5.9 | 1.5 |
| 2.5 | 74.6 | 81.2 | 6.3 | 5.9 | 1.4 |
| 4.5 | 74.5 | 81.4 | 6.3 | 6.1 | 1.3 |
| 5.5 | 74.4 | 81.2 | 6.3 | 6.1 | 1.3 |
| 6.5 | 74.5 | 81.4 | 6.3 | 6.2 | 1.2 |

[a]Feedstream: molar ratios: $C_2H_6/O_2$ = 2.3:1, $H_2/O_2$ = 2.3:1; 5% $N_2$ dilution; preheat = 275° C.; pressure = 1.35 bar abs (135 kPa); GHSV = 125,752 h$^{-1}$; flow rate = 8 slpm; autothermal process conditions; calculated adiabatic temperature = 935° C.

It was found that a magnesia monolith can be suitably employed as a support in the autothermal oxidation process of this invention.

EXAMPLE 16

(E-16)—Oxidation of Ethane to Ethylene in Modified Fluidized Bed Reactor

Alumina beads were used to prepare a catalyst. A solution containing platinum, copper, and tin in an atomic ratio of 1:5:5 was prepared by mixing hexachloroplatinic acid (0.659 ml, 0.193 M), cupric chloride (0.427 ml, 1.48 M), and stannous chloride (9.97 ml, 0.064 M, HCl to dissolve). Alumina beads (Norton, 590–850 μm, 28 g) were suspended in the solution with excess deionized water. The mixture was stirred and heated until almost all of the water was evaporated. The resulting solids were dried at 80° C. The total metals loading was 0.5 weight percent. The catalyst was loaded into the reactor and reduced under hydrogen (5 volume percent in nitrogen) at 300° C.

A reactor was used comprising a quartz tube (19 mm dia) into which the catalyst (6 g) was loaded to a bed height of 1.5 cm (static aspect ratio 0.8). A quartz frit was used to support the catalyst and evenly distribute the gas flow. The feed was preheated and the reactor insulated in the manner described hereinbefore. Ethane, hydrogen, oxygen, and nitrogen were preheated to 275° C. and fed to the reactor at a flow rate which disengaged the particles and circulated them within the bed. The flow rate was set for slightly above minimal fluidization at operating conditions (5 slpm). The bed expanded to a height of 3.0 cm (operating aspect ratio 1.6). Oxygen was introduced which resulted in catalyst ignition. Upon light-off, the catalyst operated autothermally. Process conditions and results are shown in Table 14.

TABLE 14

Autothermal Oxidation of Ethane to Ethylene
Using Modified Fluidized Bed Reactor[a]

| Time (h) | % $C_2H_6$ Conv | % $C_2H_4$ Sel | % $CH_4$ Sel | % CO Sel | % $CO_2$ Sel |
|---|---|---|---|---|---|
| 4 | 70.6 | 82.7 | 5.8 | 3.6 | 0.72 |
| 5 | 70.8 | 82.8 | 5.9 | 3.5 | 0.71 |
| 6 | 70.5 | 83.0 | 5.8 | 3.4 | 0.68 |
| 7 | 70.7 | 83.0 | 5.9 | 3.3 | 0.68 |
| 8 | 70.3 | 83.1 | 5.8 | 3.3 | 0.67 |
| 14.5[b] | 71.1 | 81.9 | 6.4 | 4.0 | 1.0 |
| 36.5[b] | 71.6 | 81.7 | 6.4 | 4.0 | 0.8 |

[a]Feedstream: molar ratios: $C_2H_6/O_2$ = 2.3:1, $H_2/O_2$ = 2.3:1; 10% $N_2$ dilution; preheat = 275° C.; pressure = 1.35 bar abs (135 kPa); GHSV = 78,600 h$^{-1}$ static bed; flow rate 5 slpm; autothermal process conditions; calculated adiabatic temperature = 975° C.
[b]Conditions as in (a), with exception of the following molar ratios: $C_2H_6/O_2$ = 2.4:1, $H_2/O_2$ = 2.2:1; calculated adiabatic temperature = 932° C.

It was seen that a reactor operating at slightly above minimal fluidization could be used for the autothermal oxidation of ethane to ethylene to achieve high selectivity to ethylene and low selectivities to methane, carbon monoxide, and carbon dioxide. In this laboratory example, the aspect ratio during operation was greater than 1:1, because of the smaller reactor diameter; however, the same results are expected with a commercial scale reactor having a diameter of 1.5 or more meters and the same bed depth of 3 cm during operation, which results in an aspect ratio less than 1:1.

EXAMPLE 17

(E-17)—Ethane Oxidation to Ethylene Using Pelleted Alumina Support in Fixed Bed Reactor The catalyst (6 g) from Example 16, prepared with alumina pellets, was evaluated in the oxidation of ethane to ethylene in a fixed bed reactor. The pellets were sandwiched between an inert alumina monolith and a quartz frit to retain the pellets in a fixed bed. Results are set forth in Table 15.

TABLE 15

Autothermal Oxidation of Ethane
to Ethylene in Fixed Bed Reactor[a]

| Time (h) | % $C_2H_6$ Conv | % $C_2H_4$ Sel | % $CH_4$ Sel | % CO Sel | % $CO_2$ Sel |
|---|---|---|---|---|---|
| 2.5 | 70.8 | 80.4 | 6.7 | 5.8 | 0.94 |
| 3.5 | 70.6 | 80.6 | 6.6 | 5.9 | 0.95 |
| 4.5 | 70.4 | 80.6 | 6.5 | 6.0 | 0.95 |
| 5.5 | 70.2 | 80.7 | 6.5 | 6.0 | 0.93 |

[a]Feedstream molar ratios: $C_2H_6/O_2$ = 2.3:1, $H_2/O_2$ = 2.3:1; 10% $N_2$ dilution; preheat, 275° C.; pressure = 1.35 bar abs (135 kPa); GHSV = 78,600 h$^{-1}$ static bed; flow rate = 5 slpm; autothermal process conditions; calculated adiabatic temperature = 960° C.

It was found that ethane could be oxidized to ethylene in a fixed bed reactor over a catalyst prepared on alumina pellets. When Example 16 was compared with Example 17, it was concluded that although both the fixed bed and the modified fluidized bed reactors were suitable, the selectivities were more favorable in the modified fluidized bed reactor. Less methane, carbon monoxide, and carbon dioxide were obtained, and more ethylene was obtained at closely similar conversions.

EXAMPLE 18

(E-18)—Ethane Oxidation Using Catalyst of Pt—Cu on Sn modified MgO Support

A magnesia monolith support (Hi-Tech Ceramics, Inc.; 17 mm dia×10 mm thick) was treated with an aqueous solution of tin (IV) chloride (0.24 M), then dried at 90° C. and reduced at about 875° C. under hydrogen (5 percent in nitrogen). Tin loading was 1 weight percent. The tin-treated support was impregnated with an aqueous solution of platinum and copper (Pt/Cu atomic ratio 1:5) prepared using solutions of hexachloroplatinic acid (0.19 M) and cupric chloride (1.49 M). Then, the monolith was dried at 80° C. and reduced at 450° C. under the aforementioned hydrogen flow. Pt loading was 3.26 weight percent.

The catalyst was evaluated in the oxidation of ethane under autothermal conditions as shown in Table 16.

TABLE 16

Ethane Oxidation Using Pt-Cu on
Sn-Treated MgO Support[a]

| TOS (h) | % Conv $C_2H_6$ | % Sel $C_2H_4$ | % Sel $CH_4$ | % Sel CO | % Sel $CO_2$ |
|---|---|---|---|---|---|
| 1.33 | 76.8 | 79.9 | 7.1 | 4.8 | 1.8 |
| 2.66 | 76.5 | 80.3 | 6.9 | 5.0 | 1.7 |
| 4.00 | 76.4 | 80.4 | 6.7 | 5.1 | 1.6 |
| 6.66 | 76.6 | 80.3 | 6.7 | 5.4 | 1.4 |
| 18.66 | 75.7 | 80.8 | 6.5 | 5.8 | 1.2 |
| 34.25 | 75.6 | 80.4 | 6.5 | 6.3 | 1.1 |
| 50.33 | 74.3 | 81.0 | 6.3 | 6.5 | 1.0 |

[a]Feedstream molar ratios: $C_2H_6/O_2$ = 2.3:1, $H_2/O_2$ = 2.3:1; 5% $N_2$ dilution; preheat, 280° C.; pressure = 1.35 bar abs (135 kPa); GHSV = 125,752 h$^{-1}$; flow rate 8 slpm; autothermal process conditions; calculated adiabatic temperature = 960° C.

It was found that the catalyst of Example 18 with a tin-modified magnesia support achieved somewhat higher conversion and higher selectivity than the related catalyst of Example 15 which used an unmodified magnesia support.

EXAMPLE 19

A solution containing nickel and copper in an atomic ratio of 1:1 was prepared from an aqueous solution of nickel (II) chloride hexahydrate (0.2 M) and an aqueous solution of copper (II) chloride (1.49 M). An alumina monolith (99.5 weight percent alumina; 17 mm diameter×10 mm length) was loaded with the Ni—Cu solution, dried at 80° C. overnight, and then reduced at 450° C. in hydrogen (5 volume percent) in nitrogen. The total metal loading was 1.48 weight percent. The catalyst was evaluated in the autothermal oxidation of ethane to ethylene in the manner previously described. The catalyst required at least 400° C. preheat for ignition. Upon ignition, the preheat was reduced, and the catalyst remained ignited under the process conditions employed; however, the catalyst extinguished in the absence of hydrogen in the feedstream.

TABLE 17

Autothermal Oxidation of Ethane Over
Ni—Cu/$Al_2O_3$ Catalyst[a,b]

| Run #19 | Time (h) | T preheat (° C.) | Mol % $C_2H_6$ Conv | Mol % $C_2H_6$ Sel | Mol % $CH_4$ Sel | Mol % CO Sel | Mol % $CO_2$ Sel |
|---|---|---|---|---|---|---|---|
| (a) | 2.5 | 250 | 79.7 | 73.2 | 7.3 | 12.3 | 1.01 |
| (b) | 3.5 | 125 | 72.9 | 75.0 | 6.2 | 11.7 | 0.90 |
| (c) | 5.5 | 200 | 64.4 | 79.6 | 5.4 | 8.7 | 0.91 |
| (d) | 7.4 | 250 | 68.4 | 78.1 | 5.9 | 9.2 | 0.94 |
| (e) | 8.2 | 275 | 69.5 | 77.7 | 6.1 | 9.3 | 0.93 |
| (f) | 17.5 | 275 | 68.6 | 76.3 | 6.6 | 10.9 | 0.59 |
| (g) | 27.0 | 275 | 68.1 | 76.2 | 6.3 | 11.4 | 0.56 |

[a]Runs 1(a), 1(b): molar ratios, $C_2H_6/O_2$ = 2.0:1; $H_2/O_2$ = 2.0:1; 9.76% $N_2$ dilution; flow rate = 7.167 slpm; GHSV = 112,658 h$^{-1}$; 1.35 bar abs; adiabatic temperature = (a) 975° C., (b) 950° C.
[b]Runs 1(c)–1(g): molar ratios, $C_2H_6/O_2$ = 2.3:1; $H_2/O_2$ = 2.3:1; 10% $N_2$ dilution; flow rate = 8.0 slpm; GHSV = 125,752 h$^{-1}$; 1.35 bar abs; adiabatic temperature = 925–975° C.

It was observed that a catalyst comprising copper and nickel on an alumina monolith is capable of oxidizing ethane to ethylene under autothermal conditions. As shown in Examples 19(a) versus 19(b) and Examples 19(c)–19(e), the catalyst is more active at a higher preheat temperature. As shown in Examples 19(e)–19(g) the catalyst is relatively stable for several hours.

What is claimed is:

1. A process of preparing an olefin comprising contacting a paraffinic hydrocarbon or a mixture of paraffinic hydrocarbons, said paraffinic hydrocarbon having from 2 to about 25 carbon atoms, with oxygen in the presence of hydrogen and a catalyst, the contacting being conducted in a reactor under autothermal process conditions sufficient to prepare a product stream containing the olefin, the catalyst comprising a platinum group metal and a least one promoter wherein the process is conducted at a temperature greater than 750° C. and less than 1,150° C.

2. The process of claim 1 wherein the paraffinic hydrocarbon comprises ethane, propane, or mixtures thereof.

3. The process of claim 1 wherein the paraffinic hydrocarbon is selected from the group consisting of naphtha, natural gas condensate, gas oils, vacuum gas oils, and mixtures thereof.

4. The process of claim 1 wherein the molar ratio of paraffinic hydrocarbon to oxygen is greater than the molar ratio of the fuel-rich, upper flammability limit.

5. The process of claim 1 wherein the molar ratio of paraffinic hydrocarbon to oxygen ranges from about 3 to about 77 times the stoichiometric ratio of hydrocarbon to oxygen for complete combustion to carbon dioxide and water.

6. The process of claim 1 wherein the molar ratio of paraffinic hydrocarbon to oxygen is greater than 0.1:1 and less than 4.0:1.

7. The process of claim 1 wherein the contacting is further carried out in the presence of a diluent.

8. The process of claim 7 wherein the diluent is selected from the group consisting of nitrogen, argon, helium, carbon dioxide, carbon monoxide, methane, and steam.

9. The process of claim 7 wherein the diluent is used in an amount greater than 0.1 mole percent and less than 70 mole percent, based on the total reactant feed including paraffin, oxygen, hydrogen, and diluent.

10. The process of claim 1 wherein the molar ratio of hydrogen to oxygen ranges from greater than 0.1:1 to less than 4.0:1.

11. The process of claim 1 wherein the platinum group metal is platinum.

12. The process of claim 1 wherein the catalyst further comprises a ceramic support.

13. The process of claim 12 wherein the ceramic support is selected from the group consisting of silica, alumina, silica-aluminas, aluminosilicates, magnesia, magnesium aluminates, magnesium silicates, zirconia, titania, boria, zirconia toughened alumina, lithium aluminum silicates, silicon carbide, and oxide-bonded silicon carbide.

14. The process of claim 13 wherein the ceramic support comprises from 65 to 100 weight percent alpha alumina or gamma alumina.

15. The process of claim 13 wherein the ceramic support is a monolith.

16. The process of claim 15 wherein the monolith is a foam having from 5 to 100 pores per linear inch (2 to 40 pores per linear cm) and a surface area greater than 0.001 $m^2/g$ and less than 10 $m^2/g$.

17. The process of claim 15 wherein the monolith is a fiber having a diameter greater than 1 micron and less than 20 microns, and a surface area greater than 0.001 $m^2/g$ and less than 1 $m^2/g$.

18. The process of claim 17 wherein the fiber monolith is a fiber mat.

19. The process of claim 1 wherein the catalyst is in a form of particles having a size between 30 and 1,000 microns.

20. The process of claim 1 wherein the promoter is selected from the group consisting of the elements of Groups 1B, 6B, 3A, 4A, and 5A of the Periodic Table and mixtures of the aforementioned elements.

21. The process of claim 1 wherein the promoter is selected from the group consisting of tin, antimony, copper, silver, indium, and mixtures thereof.

22. The process of claim 1 wherein the atomic ratio of platinum group metal to promoter ranges from greater than 1:10 to less than 1:0.5.

23. The process of claim 1 wherein the catalyst is a metallic gauze.

24. The process of claim 1 wherein the paraffinic hydrocarbon and oxygen are preheated at a temperature greater than 40° C. and less than the temperature wherein reaction of the paraffinic hydrocarbon and oxygen occurs.

25. The process of claim 24 wherein the paraffinic hydrocarbon and oxygen are preheated at a temperature greater than 200° C. and less than 900° C.

26. The process of claim 25 wherein the paraffinic hydrocarbon to oxygen molar ratio is greater than 1.5:1 and less than 4.0:1.

27. The process of claim 25 wherein the hydrogen to oxygen molar ratio is greater than 1.5:1 and less than 4.0:1.

28. The process of claim 1 wherein the process is conducted at a pressure equal to or greater than 1 atm abs (100 kPa abs) and less than 20 atm abs (2,000 kPa abs).

29. The process of claim 1 wherein the process is conducted at a gas hourly space velocity greater than 50,000 $h^{-1}$ and less than 6,000,000 $h^{-1}$.

30. The process of claim 1 wherein the process is conducted in fixed bed or fluidized bed reactor.

31. The process of claim 30 wherein the fluidized bed reactor possesses an aspect ratio less than 1:1 during operation.

32. The process of claim 31 wherein the fluidized bed reactor possesses an aspect ratio less than 1:1 in static mode.

33. The process of claim 1 wherein the olefin is converted from said paraffinic hydrocarbon or mixture of paraffinic hydrocarbons at greater than 50 mole percent.

34. The process of claim 1 wherein the percentage of carbon atoms in the paraffinic hydrocarbon or mixture of paraffinic hydrocarbons which react to form an olefin is greater than 70 carbon atom percent.

35. The process of claim 1 wherein hydrogen in said product stream is recycled to the reactor.

36. The process of claim 1 wherein methane, carbon monoxide, and/or carbon dioxide in said product stream are recycled at least in part to the reactor.

37. The process of claim 1 wherein the paraffinic hydrocarbon is ethane and the contacting is conducted under autothermal conditions at an ethane to oxygen molar ratio greater than 1.5:1 and less than 4.0:1, a hydrogen to oxygen molar ratio greater than 1.5:1 and less than 4.0:1, a gas hourly space velocity greater than 80,000 $h^{-1}$ and less than 6,000,000 $h^{-1}$, wherein optionally a diluent is used in an amount greater than 1 mole percent and less than about 70 mole percent based on the total reactant feed, wherein the platinum group metal is platinum, and the platinum group metal and promoter are supported on a magnesia or alumina ceramic support.

38. The process of claim 37 wherein the ethane and oxygen feed are preheated at a temperature in the range from 400° C. to 600° C.

39. The process of claim 37 wherein the process is conducted in a fluidized bed reactor having an aspect ratio less than 1:1 during operation.

40. The process of claim 39 wherein the catalyst has a particle size ranging between 500 and 850 microns.

41. The process of claim 37 wherein the platinum group metal and the promoter are supported on a catalyst support which is a fiber, a foam monolith, or a pellet.

42. A process for preparing an olefin comprising contacting a paraffinic hydrocarbon or a mixture of paraffinic hydrocarbons, said paraffinic hydrocarbon having from 2 to about 25 carbon atoms, with oxygen in the presence of hydrogen and a catalyst, the contacting being conducted in a reactor under autothermal process conditions sufficient to prepare a product stream containing the olefin, the catalyst comprising a platinum group metal and at least one promoter, wherein the catalyst is prepared by a process comprising pretreating a catalyst support with a support modifier, depositing the platinum group metal and at least one promoter onto the pretreated support, optionally calcining the support, and thereafter reducing the metal-loaded support.

43. The process of claim 42 wherein the catalytic support is pretreated with a support modifier selected from the group consisting of Groups 1A, 2A, 3B, 4B, 5B, 6B, 1B, 3A, 4A, 5A, the rare earth lanthanide, and the elements of the Periodic Table.

* * * * *